(12) United States Patent
Stuehr et al.

(10) Patent No.: US 6,620,616 B1
(45) Date of Patent: Sep. 16, 2003

(54) NUCLEIC ACIDS ENCODING NITRIC OXIDE SYNTHASE VARIANTS

(75) Inventors: Dennis J. Stuehr, Broadview Heights, OH (US); Subrata Adak, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/661,258

(22) Filed: Sep. 13, 2000

(51) Int. Cl.$^7$ .......................... C07H 21/04; C12N 1/20; C12N 15/74; C12N 5/02; C12N 9/02

(52) U.S. Cl. ............... 435/325; 435/252.3; 435/252.33; 435/320.1; 435/189; 536/23.2

(58) Field of Search ....................... 536/23.2; 435/252.3, 435/252.33, 320.1, 325, 189

(56) References Cited

U.S. PATENT DOCUMENTS

| | | |
|---|---|---|
| 5,132,407 A | 7/1992 | Stuehr et al. |
| 5,268,465 A | 12/1993 | Bredt et al. |
| 5,468,630 A | 11/1995 | Billiar et al. |
| 5,594,032 A | 1/1997 | Gonzalez-Cadavid et al. |
| 5,766,909 A | 6/1998 | Xie et al. |
| 5,830,848 A | 11/1998 | Harrison et al. |
| 5,834,306 A | 11/1998 | Webster et al. |
| 5,882,908 A | 3/1999 | Billiar et al. |
| 5,919,682 A | 7/1999 | Masters et al. |

OTHER PUBLICATIONS

Adak S, Crooks C, Wang Q, Crane BR, Tainer JA, Getzoff ED, Stuehr DJ. Tryptophan 409 controls the activity of neuronal nitric–oxide synthase by regulating nitric oxide feedback inhibition. J Biol Chem. Sep. 17, 1999;274(38):26907–11.*

Shimanuki T, Sato H, Daff S, Sagami I, Shimizu T. Crucial role of Lys(423) in the electron transfer of neuronal nitric–oxide synthase. J Biol Chem. Sep. 17, 1999;274(38):26956–61.*

Ausbel, F.M. et al, Current Protocols in Molecular Biology (Jan. 28, 1999) Chapter 8; Unit 8.1 http://www.mrw2.interscience.wiley.com/cponline/tserver.dll?command=doGetDoc&sUI=&database=CP&useScheme=WIS_Framed.Scheme&getDoc=cp_toc_fs.html.*

Yumoto T, Sagami I, Daff S, Shimizu T. Roles of the heme proximal side residues tryptophan409 and tryptophan421 of neuronal nitric oxide synthase in the electron transfer reaction. J Inorg Biochem. Nov. 2000;82.*

Sullivan ME, Thompson CS, Dashwood MR, Khan MA, Jeremy JY, Morgan RJ, Mikhailidis DP. Nitric oxide and penile erection: is erectile dysfunction another manifestation of vascular disease? Cardiovasc Res. Aug. 15, 1999;43(3):658–65. Review.* von der Leyen, GH Gibbons, R Morishita, NP Lewis, L Zhang et al (1995) Gene Therapy Inhibiting Neointimal Vascular Lesion: In vivo Transfer of Endothelial Cell Nitric Oxide Synthase Gene. Proc Natl Acad Sci 92: 1137–41.*

Qian H, Nepliouev V, Shetty GA, Channon KM, George SE. Nitric oxide synthase gene therapy rapidly reduces adhesion molecule expression and inflammatory cell infiltration in carotid arteries of cholesterol–fed rabbits. Circulation. Jun. 15, 1999;99(23):2979.*

"Tryptophan 409 Controls the Activity of Neuronal Nitric–oxide Synthase by Regulating Nitric Oxide Feedback Inhibition" by Adak, et al. *The Journal of Biological Chemistry*, vol. 274, No. 38, Sep. 17, 1999, pp. 26907–26911.

"Molecular Basis for Hyperactivity in Tryptophan 409 Mutants of Neuronal NO Synthase" by Adak, et al., *The Journal of Biological Chemistry*, vol. 275, No. 23, Jun. 9, 2000, pp. 17434–17439.

"A Kinetic Simulation Model that Describes Catalysis and Regulation in Nitric–Oxide Synthase" by Santolini, et al. *The Journal of Biological Chemistry*, vol. 276, 2001, pp. 1–11.

"Nitric Oxide Synthase Gene Therapy Rapidly Reduces Adhesion Molecule Expression and Inflammatory Cell Infiltration in Carotid Arteries of Cholesterol–Fed Rabbits" by Qian, et al., *Circulation*, vol. 98(18), Nov. 3, 1998, pp. 1905–1911.

"Gene therapy inhibiting neointimal vascular lesion: In vivo transfer of endothelial cell nitric oxide synthase gene" by Von Der Leyen, et al., *Proc. Natl. Acad. Sci. USA*, vol. 92, Feb. 1995, pp. 1137–1141.

"Adventitial Gene Transfer of Recombinant Endothelial Nitric Oxide Synthase to Rabbit Carotid Arteries Alters Vascular Reactivity" by Kullo, et al., *Circulation*, vol. 96, No. 7, Oct. 7, 1997, pp. 2254–2261.

"Inducible Nitric Oxide Synthase Suppresses the Development of Allograft Arteriosclerosis" by Shears, et al, *J. Clin. Invest.*, vol. 100, No. 8, Oct. 997, pp. 2035.–2042.

"Nitric Oxide Synthesis in the Lung" by Dweik, et al., *J. Clin. Invest.*, vol. 101, No. 3, Feb., 1998, pp. 660–666.

(List continued on next page.)

*Primary Examiner*—Rebecca E. Prouty
*Assistant Examiner*—Sheridan Swope
(74) *Attorney, Agent, or Firm*—Calfee, Halter & Griswold LLP

(57) ABSTRACT

Isolated polynucleotides which encode a variant of a mammalian nitric oxide synthase protein or polypeptide are provided. The variant nitric oxide synthase protein and polypeptides are substitution mutants, wherein the tryptophan that is normally located on the alpha 3 helix, six residues upstream from the cysteine which binds heme in the corresponding non-variant nitric oxide synthase protein or peptide is replaced with one of the other 19 naturally-occurring amino acid residues. The present invention also relates to vectors and recombinant cells comprising a nucleic acid which encodes a variant of a mammalian nitric oxide synthase protein. The present invention also relates to the nitric oxide synthase variant proteins and polypeptides.

16 Claims, 7 Drawing Sheets

OTHER PUBLICATIONS

"Inducible Nitric Oxide Synthase Requires both the Canonical Calmodulin–binding Domain and Additional Sequences in Order to Bind Calmodulin and Produce Nitric Oxide in the Absence of Free $Ca^{2+}$" by Ruan, et al, *The Journal of Biological Chemistry*, vol. 271, No. 37, Sep. 13, 1996, pp. 22679–22686.

"Autoinhibition of Endothelial Nitric–oxide Synthase" by Nishida, et al. *The Journal of Biological Chemistry*, vol. 274, No. 21, May 21, 1999, pp. 14692–14698.

"Identification, Characterization, and Comparison of the Calmodulin–binding Domains of the Endothelial and Inducible Nitric Oxide Synthases" by Venema, et al., *The Journal of Biological Chemistry*, vol. 271, No. 11, Mar. 15, 1996, pp. 6435–6440.

"Why Tetrahydrobiopterin?" by Mayer, et al., *Advances in Pharmacology*, vol. 34, 1995, pp. 251–261.

"Crystal Structures of Zinc–free and –bound Heme Domain of Human Inducible Nitric–oxide Synthase" by Li, et al., *The Journal of Biological Chemistry*, vol. 274, No. 30, Jul. 23, 1999, pp. 21276–21284.

"Structural characterization of nitric oxide synthaase isoforms reveals striking active–site conservation" by Fischmann, et al., *Nature Structural Biology*, vol. 6., No. 3, Mar. 1999, pp. 233–242.

"Nitric Oxide Synthases: Properties and Catalytic Mechanism" by Griffith, et al., *Annul. Rev. Physiol.*, 1995, 57:707–36.

"Nitric oxide in the sensory function of the carotid body" by Prabhakar, et al., *Brain Research*, 625(1993) 16–22.

"Adenoviral–mediated Transfer of the Human Endothelial Nitric Oxide Synthase Gene Reduces Acute Hypoxic Pulmonary Vasoconstriction in Rats" by Janssens, et al., *J. Clin. Invest.*, vol. 98, No. 2, Jul. 1996, pp. 317–324.

"Adenoviral gene transfer of nitric oxide synthase: High level expression in human vascular cells" by Channon, et al., *Cardiovascular Research*, 32 (1996) pp. 962–972.

"Altered vascular function after adenovirus–mediated overexpression of endothelial nitric oxide synthase" by Ooboshi, et al., *Gene Transfer of eNOS*, 1997, pp. H265–H270.

"Mammalian nitric oxide synthases" by Stuehr *Biochemica et Biophysica Acta*, 1411 (1999) 217–230.

\* cited by examiner

FIGURE 2

2(a): HUMAN NEURONAL NITRIC OXIDE SYNTHASE (SWISSPROT: LOCUS NOS1_HUMAN, ACCESSION P29475)(nNOS, TYPE I)

```
   1  MEDHMFGVQQ  IQPNVISVRL  FKRKVGGLGF  LVKERVSKPP  VIISDLIRGG  AAEQSGLIQA
  61  GDIILAVNGR  PLVDLSYDSA  LEVLRGIASE  THVVLILRGP  EGFTTHLETT  FTGDGTPKTI
 121  RVTQPLGPPT  KAVDLSHQPP  AGKEQPLAVD  GASGPGNGPQ  HAYDDGQEAG  SLPHANGLAP
 181  RPPGQDPAKK  ATRVSLQGRG  ENNELLKEIE  PVLSLLTSGS  RGVKGGAPAK  AEMKDMGIQV
 241  DRDLDGKSHK  PLPLGVENDR  VFNDLWGKGN  VPVVLNNPYS  EKEQPPTSGK  QSPTKNGSPS
 301  KCPRFLKVKN  WETEVVLTDT  LHLKSTLETG  CTEYICMGSI  MHPSQHARRP  EDVRTKGQLF
 361  PLAKEFIDQY  YSSIKRFGSK  AHMERLEEVN  KEIDTTSTYQ  LKDTELIYGA  KHAWRNASRC
 421  VGRIQWSKLQ  VFDARDCTTA  HGMFNYICNH  VKYATNKGNL  RSAITIFPQR  TDGKHDFRVW
 481  NSQLIRYAGY  KQPDGSTLGD  PANVQFTEIC  IQQGWKPPRG  RFDVLPLLLQ  ANGNDPELFQ
 541  IPPELVLEVP  IRHPKFEWFK  DLGLKWYGLP  AVSNMLLEIG  GLEFSACPFS  GWYMGTEIGV
 601  RDYCDNSRYN  ILEEVAKKMN  LDMRKTSSLW  KDQALVEINI  AVLYSFQSDK  VTIVDHHSAT
 661  ESFIKHMENE  YRCRGGCPAD  WVWIVPPMSG  SITPVFHQEM  LNYRLTPSFE  YQPDPWNTHV
 721  WKGTNGTPTK  RRAIGFKKLA  EAVKFSAKLM  GQAMAKRVKA  TILYATETGK  SQAYAKTLCE
 781  IFKHAFDAKV  MSMEEYDIVH  LEHETLVLVV  TSTFGNGDPP  ENGEKFGCAL  MEMRHPNSVQ
 841  EERKSYKVRF  NSVSSYSDSQ  KSSGDGPDLR  DNFESAGPLA  NVRFSVFGLG  SRAYPHFCAF
 901  GHAVDTLLEE  LGGERILKMR  EGDELCGQEE  AFRTWAKKVF  KAACDVFCVG  DDVNIEKANN
 961  SLISNDRSWK  RNKFRLTFVA  EAPELTQGLS  NVHKKRVSAA  RLLSRQNLQS  PKSSRSTIFV
1021  RLHTNGSQEL  QYQPGDHLGV  FPGNHEDLVN  ALIERLEDAP  PVNQMVKVEL  LEERNTALGV
1081  ISNWTDELRL  PPCTIFQAFK  YYLDITTPPT  PLQLQQFASL  ATSEKEKQRL  LVLSKGLQEY
1141  EEWKWGKNPT  IVEVLEEFPS  IQMPATLLLT  QLSLLQPRYY  SISSSPDMYP  DEVHLTVAIV
1201  SYRTRDGEGP  IHHGVCSSWL  NRIQADELVP  CFVRGAPSFH  LPRNPQVPCI  LVGPGTGIAP
1261  FRSFWQQRQF  DIQHKGMNPC  PMVLVFGCRQ  SKIDHIYREE  TLQAKNKGVF  RELYTAYSRE
1321  PDKPKKYVQD  ILQEQLAESV  YRALKEQGGH  IYVCGDVTMA  ADVLKAIQRI  MTQQGKLSAE
1381  DAGVFISRMR  DDNRYHEDIF  GVTLRTYEVT  NRLRSESIAF  IEESKKDTDE  VFSS
```

FIGURE 2 continued

2(b): RAT NEURONAL NITRIC OXIDE SYNTHASE (SWISSPROT:
LOCUS NOS1_RAT, ACCESSION P29476) (nNOS, TYPE I)

```
   1   MEENTFGVQQ  IQPNVISVRL  FKRKVGGLGF  LVKERVSKPP  VIISDLIRGG  AAEQSGLIQA
  61   GDIILAVNDR  PLVDLSYDSA  LEVLRGIASE  THVVLILRGP  EGFTTHLETT  FTGDGTPKTI
 121   RVTQPLGPPT  KAVDLSHQPS  ASKDQSLAVD  RVTGLGNGPQ  HAQGHGQGAG  SVSQANGVAI
 181   DPTMKSTKAN  LQDIGEHDEL  LKEIEPVLSI  LNSGSKATNR  GGPAKAEMKD  TGIQVDRDLD
 241   GKSHKAPPLG  GDNDRVFNDL  WGKDNVPVIL  NNPYSEKEQS  PTSGKQSPTK  NGSPSRCPRF
 301   LKVKNWETDV  VLTDTLHLKS  TLETGCTEHI  CMGSIMLPSQ  HTRKPEDVRT  KDQLFPLAKE
 361   FLDQYYSSIK  RFGSKAHMDR  LEEVNKEIES  TSTYQLKDTE  LIYGAKHAWR  NASRCVGRIQ
 421   WSKLQVFDAR  DCTTAHGMFN  YICNHVKYAT  NKGNLRSAIT  IFPQRTDGKH  DFRVWNSQLI
 481   RYAGYKQPDG  STLGDPANVQ  FTEICIQQGW  KAPRGRFDVL  PLLLQANGND  PELFQIPPEL
 541   VLEVPIRHPK  FDWFKDLGLK  WYGLPAVSNM  LLEIGGLEFS  ACPFSGWYMG  TEIGVRDYCD
 601   NSRYNILEEV  AKKMDLDMRK  TSSLWKDQAL  VEINIAVLYS  FQSDKVTIVD  HHSATESFIK
 661   HMENEYRCRG  GCPADWVWIV  PPMSGSITPV  FHQEMLNYRL  TPSFEYQPDP  WNTHVWKGTN
 721   GTPTKRRAIG  FKKLAEAVKF  SAKLMGQAMA  KRVKATILYA  TETGKSQAYA  KTLCEIFKHA
 781   FDAKAMSMEE  YDIVHLEHEA  LVLVVTSTFG  NGDPPENGEK  FGCALMEMRH  PNSVQEERKS
 841   YKVRFNSVSS  YSDSRKSSGD  GPDLRDNFES  TGPLANVRFS  VFGLGSRAYP  HFCAFGHAVD
 901   TLLEELGGER  ILKMREGDEL  CGQEEAFRTW  AKKVFKAACD  VFCVGDDVNI  EKPNNSLISN
 961   DRSWKRNKFR  LTYVAEAPDL  TQGLSNVHKK  RVSAARLLSR  QNLQSPKFSR  STIFVRLHTN
1021   GNQELQYQPG  DHLGVFPGNH  EDLVNALIER  LEDAPPANHV  VKVEMLEERN  TALGVISNWK
1081   DESRLPPCTI  FQAFKYYLDI  TTPPTPLQLQ  QFASLATNEK  EKQRLLVLSK  GLQEYEEWKW
1141   GKNPTMVEVL  EEFPSIQMPA  TLLLTQLSLL  QPRYYSISSS  PDMYPDEVHL  TVAIVSYHTR
1201   DGEGPVHHGV  CSSWLNRIQA  DDVVPCFVRG  APSFHLPRNP  QVPCILVGPG  TGIAPFRSFW
1261   QQRQFDIQHK  GMNPCPMVLV  FGCRQSKIDH  IYREETLQAK  NKGVFRELYT  AYSREPDRPK
1321   KYVQDVLQEQ  LAESVYRALK  EQGGHIYVCG  DVTMAADVLK  AIQRIMTQQG  KLSEEDAGVF
1381   ISRLRDDNRY  HEDIFGVTLR  TYEVTNRLRS  ESIAFIEESK  KDADEVFSS
```

FIGURE 2 continued

2(c): HUMAN ENDOTHELIAL NITRIC OXIDE SYNTHASE (SWISSPROT: LOCUS NOS3_HUMAN, ACCESSION P29474) (eNOS, TYPE III)

```
   1  MGNLKSVAQE  PGPPCGLGLG  LGLGLCGKQG  PATPAPEPSR  APASLLPPAP  EHSPPSSPLT
  61  QPPEGPKFPR  VKNWEVGSIT  YDTLSAQAQQ  DGPCTPRRCL  GSLVFPRKLQ  GRPSPGPPAP
 121  EQLLSQARDF  INQYYSSIKR  SGSQAHEQRL  QEVEAEVAAT  GTYQLRESEL  VFGAKQAWRN
 181  APRCVGRIQW  GKLQVFDARD  CRSAQEMFTY  ICNHIKYATN  RGNLRSAITV  FPQRCPGRGD
 241  FRIWNSQLVR  YAGYRQQDGS  VRGDPANVEI  TELCIQHGWT  PGNGRFDVLP  LLLQAPDEPP
 301  ELFLLPPELV  LEVPLEHPTL  EWFAALGLRW  YALPAVSNML  LEIGGLEFPA  APFSGWYMST
 361  EIGTRNLCDP  HRYNILEDVA  VCMDLDTRTT  SSLWKDKAAV  EINVAVLHSY  QLAKVTIVDH
 421  HAATASFMKH  LENEQKARGG  CPADWAWIVP  PISGSLTPVF  HQEMVNYFLS  PAFRYQPDPW
 481  KGSAAKGTGI  TRKKTFKEVA  NAVKISASLM  GTVMAKRVKA  TILYGSETGR  AQSYAQQLGR
 541  LFRKAFDPRV  LCMDEYDVVS  LEHETLVLVV  TSTFGNGDPP  ENGESFAAAL  MEMSGPYNSS
 601  PRPEQHKSYK  IRFNSISCSD  PLVSSWRRKR  KESSNTDSAG  ALGTLRFCVF  GLGSRAYPHF
 661  CAFARAVDTR  LEELGGERLL  QLGQGDELCG  QEEAFRGWAQ  AAFQAACETF  CVGEDAKAAA
 721  RDIFSPKRSW  KRQRYRLSAQ  AEGLQLLPGL  IHVHRRKMFQ  ATIRSVENLQ  SSKSTRATIL
 781  VRLDTGGQEG  LQYQPGDHIG  VCPPNRPGLV  EALLSRVEDP  PAPTEPVAVE  QLEKGSPGGP
 841  PPGWVRDPRL  PPCTLRQALT  FFLDITSPPS  PQLLRLLSTL  AEEPREQQEL  EALSQDPRRY
 901  EEWKWFRCPT  LLEVLEQFPS  VALPAPLLLT  QLPLLQPRYY  SVSSAPSTHP  GEIHLTVAVL
 961  AYRTQDGLGP  LHYGVCSTWL  SQLKPGDPVP  CFIRGAPSFR  LPPDPSLPCI  LVGPGTGIAP
1021  FRGFWQERLH  DIESKGLQPT  PMTLVFGCRC  SQLDHLYRDE  VQNAQQRGVF  GRVLTAFSRE
1081  PDNPKTYVQD  ILRTELAAEV  HRVLCLERGH  MFVCGDVTMA  TNVLQTVQRI  LATEGDMELD
1141  EAGDVIGVLR  DQQRYHEDIF  GLTLRTQEVT  SRIRTQSFSL  QERQLRGAVP  WAFDPPGSDT
1201  NSP
```

FIGURE 2 continued

2(d): HUMAN INDUCIBLE NITRIC OXIDE SYNTHASE (EC 1.14.13.39), AIRWAY EPITHELIUM (iNOS, TYPE II)

```
1     MACPWKFLFK TKFHQYAMNG EKDINNNVEK APCATSSPVT QDDLQYHNLS KQQNESPQPL
61    VETGKKSPES LVKLDATPLS SPRHVRIKNW GSGMTFQDTL HHKAKGILTC RSKSCLGSIM
121   TPKSLTRGPR DKPTPPDELL PQAIEFVNQY YGSFKEAKIE EHLARVEAVT KEIETTGTYQ
181   LTGDELIFAT KQAWRNAPRC IGRIQWSNLQ VFDARSCSTA REMFEHICRH VRYSTNNGNI
241   RSAITVFPQR SDGKHDFRVW NAQLIRYAGY QMPDGSIRGD PANVEFTQLC IDLGWKPKYG
301   RFDVVPLVLQ ANGRDPELFE IPPDLVLEVA MEHPKYEWFR ELELKWYALP AVANMLLEVG
361   GLEFPGCPFN GWYMGTEIGV RDFCDVQRYN ILEEVGRRMG LETHKLASLW KDQAVVEINI
421   AVLHSFQKQN VTIMDHHSAA ESFMKYMQNE YRSRGGCPAD WIWLVPPMSG SITPVFHQEM
481   LNYVLSPFYY YQVEAWKTHV WQDEKRRPKR REIPLKVLVK AVLFACMLMR KTMASRVRVT
541   ILFATETGKS EALAWDLGAL FSCAFNPKVV CMDKYRLSCL EEERLLLVVT STFGNGDCPG
601   NGEKLKKSLF MLKELNNKFR YAVFGLGSSM YPRFCAFAHD IDQKLSHLGA SQLTPMGEGD
661   ELSGQEDAFR SWAVQIFKAA CETFDVRGKQ HIQIPKLYTS NVTWDPHHYR LVQDSQPLDL
721   SKALSSMHAK NVFTMRLKSR QNLQSPTSSR ATILVELSCE DGQGLNYLPG EHLGVCPGNQ
781   PALVQGILER VVDGPTPHQT VRLEALDESG SYWVSDKRLP PCSLSQALTY FLDITTPPTQ
841   LLLQKLAQVA TEEPERQRLE ALCQPSEYSK WKFTNSPTFL EVLEEFPSLR VSAGFLLSQL
901   PILKPRFYSI SSSRDHTPTE IHLTVAVVTY HTGDGQGPLH HGVCSTWLNS LKPQDPVPCF
961   VRNASAFHLP EDPSHPCILI GPGTGIAPFR SFWQQRLHDS QHKGVRGGRM TLVFGCRRPD
1021  EDHIYQEEML EMAQKGVLHA VHTAYSRLPG KPKVYVQDIL RQQLASEVLR VLHKEPGHLY
1081  VCGDVRMARD VAHTLKQLVA AKLKLNEEQV EDYFFQLKSQ KRYHEDIFGA VFPYEAKKDR
1141  VAVQPSSLEM SAL //
```

FIGURE 2 continued

2(e):  MOUSE INDUCIBLE NITRIC OXIDE SYNTHASE (SWISSPROT
       LOCUS NOS2_MOUSE, ACCESSION P29477)(iNOS, TYPE II)

```
   1   MACPWKFLFK VKSYQSDLKE EKDINNNVKK TPCAVLSPTI QDDPKSHQNG SPQLLTGTAQ
  61   NVPESLDKLH VTSTRPQYVR IKNWGSGEIL HDTLHHKATS DFTCKSKSCL GSIMNPKSLT
 121   RGPRDKPTPL EELLPHAIEF INQYYGSFKE AKIEEHLARL EAVTKEIETT GTYQLTLDEL
 181   IFATKMAWRN APRCIGRIQW SNLQVFDARN CSTAQEMFQH ICRHILYATN NGNIRSAITV
 241   FPQRSDGKHD FRLWNSQLIR YAGYQMPDGT IRGDAATLEF TQLCIDLGWK PRYGRFDVLP
 301   LVLQADGQDP EVFEIPPDLV LEVTMEHPKY EWFQELGLKW YALPAVANML LEVGGLEFPA
 361   CPFNGWYMGT EIGVRDFCDT QRYNILEEVG RRMGLETHTL ASLWKDRAVT EINVAVLHSF
 421   QKQNVTIMDH HTASESFMKH MQNEYRARGG CPADWIWLVP PVSGSITPVF HQEMLNYVLS
 481   PFYYYQIEPW KTHIWQNEKL RPRRREIRFR VLVKVVFFAS MLMRKVMASR VRATVLFATE
 541   TGKSEALARD LATLFSYAFN TKVVCMDQYK ASTLEEEQLL LVVTSTFGNG DCPSNGQTLK
 601   KSLFMLRELN HTFRYAVFGL GSSMYPQFCA FAHDIDQKLS HLGASQLAPT GEGDELSGQE
 661   DAFRSWAVQT FRAACETFDV RSKHHIQIPK RFTSNATWEP QQYRLIQSPE PLDLNRALSS
 721   IHAKNVFTMR LKSQQNLQSE KSSRTTLLVQ LTFEGSRGPS YLPGEHLGIF PGNQTALVQG
 781   ILERVVDCPT PHQTVCLEVL DESGSYWVKD KRLPPCSLSQ ALTYFLDITT PPTQLQLHKL
 841   ARFATDETDR QRLEALCQPS EYNDWKFSNN PTFLEVLEEF PSLHVPAAFL LSQLPILKPR
 901   YYSISSSQDH TPSEVHLTVA VVTYRTRDGQ GPLHHGVCST WIRNLKPQDP VPCFVRSVSG
 961   FQLPEDPSQP CILIGPGTGI APFRSFWQQR LHDSQHKGLK GGRMSLVFGC RHPEEDHLYQ
1021   EEMQEMVRKR VLFQVHTGYS RLPGKPKVYV QDILQKQLAN EVLSVLHGEQ GHLYICGDVR
1081   MARDVATTLK KLVATKLNLS EEQVEDYFFQ LKSQKRYHED IFGAVFSYGA KKGSALEEPK
1141   ATRL
```

US 6,620,616 B1

NUCLEIC ACIDS ENCODING NITRIC OXIDE SYNTHASE VARIANTS

This invention was made at least in part with government support under National Institutes of Health Grant GM5 1491. The government has certain rights in the invention.

BACKGROUND

The free radical nitric oxide (NO) is a chemical messenger that is involved in regulating blood pressure, homeostasis, platelet aggregation, immuno-integrity and neurotransmission. NO is produced in many cell types, including endothelial cells, neurons, airway epithelial cells and macrophages. In blood vessels, NO mediates endothelium-dependent vasodilation. NO is also involved in maintaining basal vascular tone and regulating regional blood flow. In the nervous system NO plays a role in neurotransmission, synaptic plasticity, peristalsis, penile erection, neuro-degenerative disease, and excitotoxicity. In the immune system, NO is produced by activated macrophages and neutrophils as a cytotoxic agent against tumor cells and pathogens.

The formation of NO is catalyzed by a family of enzymes termed nitric oxide synthases. The nitric oxide synthases (NOSs) are encoded by three different genes. Two of the genes encode isoforms that bind calmodulin in a reversible $Ca^{2+}$ dependent manner. These two isoforms are known as neuronal NOS (nNOS) or NOS I and endothelial NOS (eNOS) or NOS III. nNOS and eNOS are constitutively expressed. nNOS and eNOS have approximately 55% amino acid sequence identity. The third gene encodes an inducible isoform known as inducible NOS (iNOS) or NOS II. iNOS is constitutively expressed only in select tissues such as lung epithelium, and is more typically synthesized in response to inflammatory or pro-inflammatory mediators. Each NOS is comprised of an N-terminal oxygenase domain and a C-terminal reductase domain, with a $Ca^{2+}$— calmodulin (CaM) binding region of approximately 30 amino acids located between the two domains. (See FIG. 1.)

Recent studies have shown that in vivo gene transfer of polynucleotides encoding different NOS isoforms may represent a therapeutic strategy for diseases characterized by decreased bioavailability of NO, such as vascular diseases. Specifically, Lloyd-Jones and Bloch have shown that gene therapy employing an nNOS-expressing adenoviral vector increased the sensitivity of a normal rabbit's carotid arteries to acetylcholine and also reversed the deficit in endothelium-dependent vascular relaxation in cholesterol-fed rabbits. (Lloyd-Jones and Bloch (1996) *Annual Rev. Med.* 47:365–75.) Quian et. al. showed that in vivo transfer of the nNOS gene into cholesterol-fed rabbits reduced vascular adhesion molecule expression, lipid deposition, and inflammatory cell infiltration in the carotid arteries of such animals. (Qian, et. al. (1999) *Circulation* 98, 2979–2982.) Von der Leyen et al have shown that in vivo transfer of an eNOS-expressing plasmid to balloon denuded rat carotids significantly limited the subsequent development of neointimal hyperplasia. The eNOS-expressing plasmids were delivered via a liposome-Sendai virus hemagglutinin protein complex. (Von der Leyen, et. al. (1995) *PNAS* 92:1137–1141.) Kullo et al showed that adenovirus-mediated transfer of the gene for eNOS to the adventitia of rabbit carotid arteries had a favorable effect on vascular reactivity (Kullo, et. al. (1996) *Circulation* 96:7, 2254–2261.) Shears et al have shown that in vivo transfer of an adenovirus expressing iNOS reduced vasculopathy in rat aortic allografts. (Shears, et. al. (1997) *J. Clin. Invest.* 100:8, 2035–2042.) Thus, all three major NOS isoforms appear to be reasonable candidates for in vivo applications to achieve or augment NO production.

Accordingly, it is desirable to have polynucleotides which encode NOS. It is especially desirable to have polynucleotides which encode NOS proteins or polypeptides that are fully active at all possible intracellular concentrations of $O_2$.

SUMMARY OF THE INVENTION

The present invention provides polynucleotides which encode variants of NOS. The "NOS variant" comprises a substitution mutant, wherein the tryptophan that is normally located on the alpha 3 helix, six residues upstream from the cysteine which binds heme in the corresponding non-variant NOS, is replaced with one of the other 19 naturally-occurring amino acid residues. Preferably, the targeted tryptophan is replaced with an amino acid residue that forms no or weaker hydrogen bonds with the NOS heme thiolate.

The present invention also relates to vectors and recombinant cells comprising a nucleic acid which encodes a NOS variant. The present invention also relates to NOS variant proteins and polypeptides.

BRIEF DESCRIPTION OF THE FIGURES

FIG. 2 depicts representative sequences of NOS showing the location of the heme-binding cysteine and the un-substituted tryptophan: 2(a) Human nNOS, SEQ ID NO: 1; 2(b) Rat nNOS; SEQ ID NO:2; 2(c) Human eNOS, SEQ ID NO:3; 2(d) Human iNOS, SEQ ID NO:4; 2(e) Mouse iNOS, SEQ ID NO: 5.

DETAILED DESCRIPTION OF THE INVENTION

The present invention provides polynucleotides which encode a nitric oxide synthase variant. The variant is a mutant nNOS, iNOS, eNOS protein or polypeptide, wherein the tryptophan which is normally located within the alpha 3 helix, six residues upstream from the heme binding cysteine in the non-variant NOS protein or polypeptide (hereinafter referred to as the "targeted residue") is substituted with a different amino acid, i.e., with one of the other 19 naturally-occurring amino acids. Preferably, the tryptophan is substituted with an amino acid which would form weaker hydrogen bonds or no hydrogen bonds with the heme thiolate. Amino acids which would not form hydrogen bonds with the heme thiolate are alanine, valine, leucine, isoleucine, phenylalanine, and glycine. Amino acids which would form weaker hydrogen bonds with the heme thiolate than tryptophan are proline, methionine, serine, threonine, cysteine, tyrosine, asparagine, glutamine, aspartic acid, glutamic acid, lysine, arginine, and histidine. Tyrosine and phenylalanine are also able to preserve the aromatic stacking between the targeted residue and the porphyrin ring, and are, thus, especially well-suited as substitutes for the targeted residue.

Figure 1:
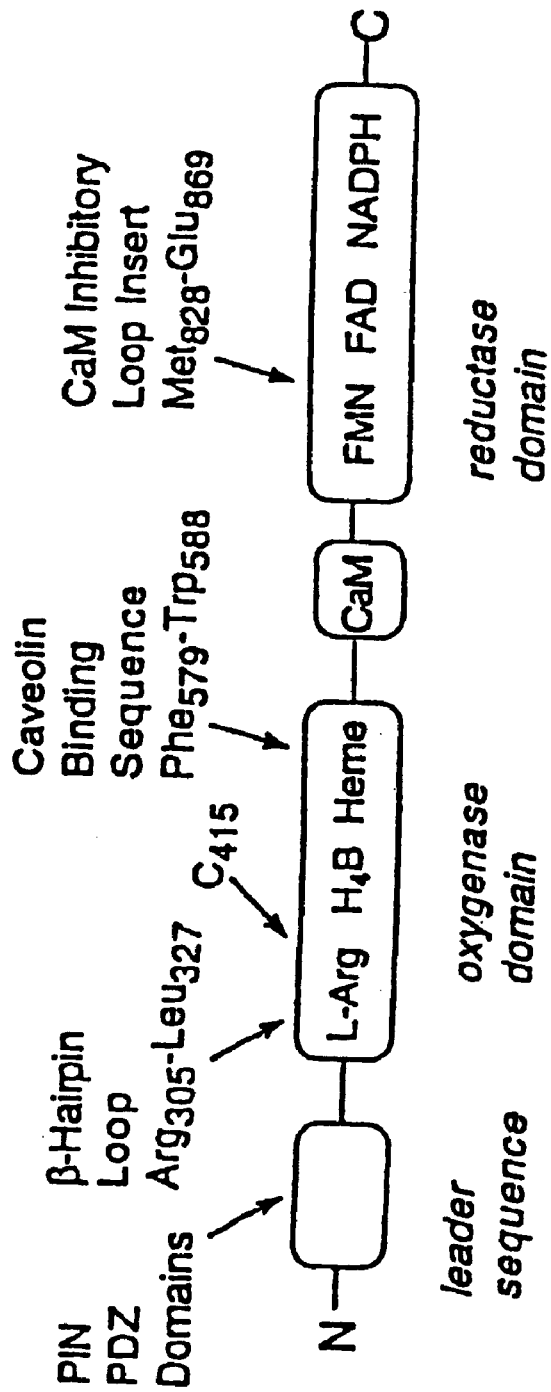
FIG. 1 is schematic representation of the domain arrangement of rat nNOS.

As used herein the term NOS variant encompasses full-length NOS protein variants. As used herein the term NOS variant also encompasses truncated NOS protein variants which lack a portion or all of the leader sequence, i.e., the sequence which is linked to the N-terminal amino acid residue of the core region of the oxygenase domain. The leader sequence in the known iNOS forms is about 76 amino acid residues in length. The leader sequence in the known nNOS forms is about 240 amino acid residues in length. The leader sequence in the known eNOS forms is about 65 amino acid residues in length. The core region of the oxygenase domain binds heme, tetrahydrobiopterin ($H_4B$), and L-Arg, and forms the active site where NO synthesis takes place. As shown in FIG. 1, a β hairpin loop is located at the N-terminus of the core region of the oxygenase domain in all NOS forms. The reductase domain contains the NADPH binding site in all NOS forms, and the auto-inhibitory loop in the nNOS and eNOS forms.

The NOS variant proteins and polypeptides of the present invention catalyze in vitro formation of NO at rates that are faster than the corresponding non-variant NOS protein or polypeptide at $O_2$ levels ranging from 0 to 230 mm $O_2$. Advantageously, the difference in the enzymatic activity of the NOS variant and the corresponding non-variant NOS is even more pronounced at low concentrations of $O_2$, i.e., concentrations ranging from 0 to 50 μM. Thus, the NOS variant is particularly useful for generating NO in cells that have low levels of intracellular $O_2$. Such cells are found in normal tissues and in tissues experiencing hypoxia, such as occurs in many tumors, during stroke or during surgical occlusion. Low levels of intracellular $O_2$ are also found in tissues that have sub-optimal circulation and $O_2$ delivery due to age or disease. A 90 correlation between in vitro and in vivo NOS activity has been shown for all three NOS isoforms. (See Dweik, et. al. (1998) J. Clin. Invest. 101:3, 660–666; Griffith and Stuehr (1995) Annu. Rev. Physiol. 57:707–736)

Optionally, the NOS variant is able to bind calmodulin at all intracellular levels of calcium. The iNOS proteins and peptides have this feature, while the nNOS and eNOS proteins can be modified to have such feature. Mutant nNOS proteins which are calcium independent and methods for generating polynucleotides which encode such mutant proteins are described in Ruan, et. al. (1996) J. Biol. Chem. 271:37, 22679–22686, which is specifically incorporated herein by reference. Mutant eNOS proteins which are calcium independent and methods for generating polynucleotides which encode such mutant proteins are described in Venema, et. al. (1996) J. Biol. Chem. 271:11, 6435–6440; and Nishida, et. al. (1999) J. Biol. Chem. 274:21, 14692–14698, all of which are specifically incorporated herein by reference.

The term NOS variant encompasses mutant NOS proteins and polypeptides that, except for the substitution at the targeted residue, have a wild-type sequence. The term NOS variant also encompasses multiple mutant NOS variant proteins and polypeptides that have additional mutations in the wild-type sequence, i.e., in addition to the substitution at the targeted residue. These additional mutations may be substitutions, additions, or deletions. Favorable additional mutations would include those that render eNOS and nNOS $Ca^{2+}$ independent. Such mutations could be achieved by replacing residues in the nNOS or eNOS CaM site with residues specific for the iNOS calmodulin binding site. Alternatively, $Ca^{2+}$ concentration independence could be achieved by deletion of the auto-inhibitory loop present in the reductase domain of the nNOS and eNOS forms. (See Daff, et. Al. (1999) J. Biol. Chem. 274:30589–30595; Nishida, et. al. (1999) J. Biol. Chem. 274:14692–14698.)

Another favorable mutation that would augment NOS activity would be substitution with aspartic acid (Asp) of the serine residue that is present in the nNOS and eNOS NADPH binding module of the reductase domain. Mutation to Asp mimics phosphorylation of the serine residue and appears to increase enzyme activity by an unknown mechanism. (See Busse, et. al. (1999) Nature (1999) 399: 601–5; Sessa, et. al. (1999) Nature (1999) 399: 597–601. Another favorable mutation would be mutation, truncation, or deletion of the leader sequence in nNOS, resulting in altered cellular positioning of the enzyme which may increase NO production. Other favorable mutations would be those that would increase the rate of heme reduction through modifications in the reductase or oxygenase domains, thus increasing NO synthesis.

Preferably, the NOS variants which are multiple mutants, i.e., the NOS variants which have mutations in addition to the substitution at the targeted residue, have an amino acid sequence which is at least 90%, more preferably at least 95%, most preferably at least 99% identical to a wild-type nNOS, iNOS or eNOS polypeptide or protein. The multiple mutant NOS variant has an in vitro enzymatic activity which is equal to or greater than the lesser of the in vitro enzymatic activity of the wild-type NOS or the in vitro enzymatic activity of the corresponding mutant NOS form which lacks a mutation of the targeted residue. Preferably, enzymatic activity is determined by in vitro measurement of NO production.

Sequences which are at least 90% identical to a wild-type NOS sequence have no more than 10 alterations, i.e. any combination of deletions, insertions or substitutions, per 100 amino acids of the reference amino acid sequence. Percent identity may be determined by comparing the amino acid sequence of the NOS variant multiple mutant with the NOS wild-type sequence using MEGALIGN project in the DNA STAR program. The NOS variant multiple mutant sequences and NOS wild-type sequences are aligned for identity calculations using the method of the software basic local alignment search tool in the BLAST network service (the National Center for Biotechnology Information, Bethesda, Md.) which employs the method of Altschul, S. F., Gish, W., Miller, W., Myers, E. W. & Lipman, D. J. (1990) J. Mol. Biol. 215, 403–410. Identities are calculated, for example, by the Align program (DNAstar, Inc.) In all cases, internal gaps and amino acid insertions in the candidate sequence as aligned are not ignored when making the identity calculation.

In the multiple mutant NOS variant, it is preferred that the residues other than the targeted residue be substituted with a conservative amino acid, however, it is possible to substitute non-conservative amino acids for the residues other than the targeted residue. In conservative amino acid substitutions, the substituted amino acid shares similar structural or chemical properties with the corresponding amino acid in the reference sequence. By way of example, conservative amino acid substitutions involve substitution of one aliphatic or hydrophobic amino acid, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Preparation of the Polynucleotides Which Encode the NOS Variants.

The single mutant NOS variants and multiple mutant NOS variants may be made by site-directed mutagenesis of a polynucleotide which encodes the non-variant NOS protein or polypeptide, i.e., the wild-type NOS protein or polypeptide. The multiple mutant NOS may also be made by replacing regions of the wild-type or variant eNOS or nNOS forms with iNOS regions, or deleting regions of the wild-type or variant eNOS or nNOS forms that regulate calcium concentration dependence. Methods which are employed to modify a polynucleotide by replacing one codon with another codon are well-known in the art. Such methods are described in Adak, et. al. (1999) *J. Biol. Chem.* 274:38, 26907–26911, which is specifically incorporated herein by reference.

Polynucleotides and Constructs

The present invention provides isolated polynucleotides and recombinant DNA constructs which encode single mutant NOS variants and multiple mutant NOS variants.

As used herein, the term "polynucleotide" is intended to refer to DNA or RNA molecules that have been isolated free from total genomic or total cellular nucleic acids. Included within the term polynucleotide are segments of NOS variant genes which may be employed in the preparation of vectors, as well as the vectors themselves. It will be understood that the present invention also encompasses sequences which are complementary to the sequences listed herein, single stranded, double stranded, and triple stranded versions thereof, along with biological functional equivalents thereof, including naturally occurring variants and genetically engineered mutants.

As used herein, "vector" is defined as a recombinantly produced DNA construct that comprises a polynucleotide to be delivered into a host cell, either in vivo, ex vivo or in vitro. Recombinant constructs comprise one or more polynucleotide sequences, including the polynucleotide which encodes the NOS variant protein or polypeptide operatively linked to an expression control sequence, i.e., a promoter, which directs mRNA synthesis. A "promoter" is defined as a DNA sequence that directs RNA polymerase to bind to DNA and initiate RNA synthesis. A strong promoter is one which causes transcription of mRNAs to be initiated at high frequency. The promoter may be one that is naturally associated with NOS gene isoforms, e.g., in human cells, as may be obtained by isolating the 5' non-coding sequences located upstream of the coding segment or exon, for example, using recombinant cloning and/or PCR technology. The promoter may also be in the form of a recombinant or heterologous promoter that is not normally associated with a NOS gene in its natural environment. Optionally, the expression vector may employ a promoter that is cell or tissue specific. Further, a promoter may be constitutively active, or it may be selectively activated by certain substances (e.g., a tissue-specific factor), under certain conditions (e.g., hypoxia, or the presence of an enhancer element in the chimeric gene containing the promoter), or during certain developmental stages of the organism (e.g., active in fetus, silent in adult). The promoters employed may be used under appropriate conditions to direct high level expression of the NOS variant polynucleotide, such as is advantageous in the large-scale production of recombinant proteins or peptides. Representative examples of such promoters include the LTR or SV40 promoter, the *E. coli* lac or trp, lac UV5, the phage lambda PL promoter, T7 or T3, and other promoters known to control expression of genes in prokaryotic or eukaryotic cells or in viruses.

Preferably, the expression vector also contains an origin of replication for autonomous replication in host cells, selectable markers (for example, the ampicillin resistance gene of *E.coli*,) to permit selection of transformed cells, i.e., cells that are expressing the heterologous DNA sequences, a limited number of useful restriction enzyme sites, a ribosome binding site for translation initiation, sequences for the termination of transcription such as polyadenylated segments in the untranslated portion of the mRNA, a potential for high copy number, and active promoters. The polynucleotide sequence encoding the NOS variant protein or polypeptide is incorporated into the vector in frame with translation initiation and termination sequences.

Examples of expression vectors are chromosomal, non-chromosomal and synthetic DNA sequences, e.g., derivatives of SV40, bacterial plasmids, phage DNAs, yeast plasmids, vectors derived from combinations of plasmids and phage DNAs, viral DNA such as vaccinia, adenovirus, fowl pox virus, pseudorabies, baculovirus, and retrovirus. Expression vectors may include, but are not limited to, cloning vectors, modified cloning vectors, specifically designed plasmids or viruses. A variety of mammalian expression vectors may be used to express NOS variant in mammalian cells. In the present invention, pLNCX is a preferred vector due to the presence of CLA1 site useful for NOS variant polynucleotide insertion.

Optionally, the vector comprises a sequences which codes for GTP cyclohydrolase. GTP cyclohydrolase is responsible for biosynthesis of $H_4B$, an essential cofactor for all wild-type and NOS variant isoforms.

Uses for the NOS Variant Polynucleotide

The NOS variant polynucleotides are useful for producing NOS variant protein or polypeptide. For example, an RNA molecule encoding a variant nNOS polypeptide is used in a cell-free translation systems to prepare such polypeptide. Alternatively, a DNA molecule encoding a NOS variant protein or polypeptide is introduced into an expression vector and used to transform cells for study in cultured cell systems, or to augment NO production in living tissue through in vivo or ex vivo administration.

A. Use of Polynucleotides to Produce NOS Variant Proteins or Polypeptides

RNA molecules derived from DNA constructs that encode the NOS variant proteins and polypeptides may be used to produce NOS variant proteins and polynucleotides in cell-free translation systems. Alternatively, the NOS variant proteins and polynucleotides are made by transfecting host cells with expression vectors that comprise a DNA sequence that encodes the respective NOS variant proteins and polynucleotides and then inducing expression of the protein in the host cells. For recombinant production, recombinant constructs comprising one or more of the sequences which encode the NOS variant proteins and polypeptides are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

Suitable host cells include, for example, mammalian cells, yeast, bacteria, or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the NOS variant proteins and polynucleotides.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate recombinant NOS variant proteins and polynucleotides.

The polynucleotides encoding a NOS variant protein or polypeptide are used to express recombinant protein using conventional techniques. Such techniques are described in Sambrook, J. et al (1989) Molecular Cloning A Laboratory Manual, Cold Spring Harbor Press, Plainview, N.Y. and Ausubel, F. M. et al. (1989) Current Protocols in Molecular Biology, John Wiley & Sons, New York, N.Y., which is specifically incorporated herein by reference.

Use of Polynucleotides in Cultured Cells

The polynucleotides encoding the NOS variant protein or polypeptide are used to alter the production of NO in cultured cells. Such cells are useful for studying the intracellular effects of NO. Preferably, transformed human kidney epithelial cell line R293 are used for transfection with a pLNCX vector comprising NOS variant polynucleotides.

Recombinant constructs comprising one or more of the sequences which encode the NOS variant proteins and polypeptides are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection. Preferably, the recombinant construct also comprises a reporter gene. The particular reporter molecule which can be employed in the present invention is not critical. Examples of such reporter molecules which can be employed in the present invention are well-known in the art and include beta.-galactosidase (Fowler, et al, (1977) *Proc. Natl. Acad. Sci.*, 74:1507), luciferase (Tu et al, *Biochem.* (1975) 14:1970), and chloramphenicol acetyltransferase (Gorman et al, (1982) *Mol. Cell Biol.*, 2:1044–1051). Preferably, another polynucleotide encoding GTP cyclohydrolase is also included in the same or a separate construct.

Preferably, the recombinant construct or vector is first used to transform *E. coli*, then colonies are screened to select those cells that contain plasmid with the NOS variant polynucleotide in the correct orientation, as determined by restriction digest analysis. Thereafter, the vector comprising the NOS variant polynucleotide is grown up in larger amounts using the *E. coli*, purified, and then transfected into appropriate host cells using conventional procedures. Stable transfectant cell lines are selected and screened for levels of expression of NOS variant polypeptides preferably by assaying for NO synthesis activity using standard cell lysate assay. The cell line exhibiting the highest NO synthesis activity per mg of soluble protein is useful for evaluating NO synthesis versus $O_2$ concentration measurements or the effect of high levels of NO on cellular processes.

Use of Polynucleotides to Augment NO Production In Vivo

The polynucleotides of the present invention can be used to achieve or augment expression of NOS variant proteins or polypeptides in vivo and thereby increase NO production in target tissue, including vascular tissue, tumor tissue, tissue of the nervous system, including brain, penile and uterine tissue, and lung tissue. NOS variant expression is desirable where nitric oxide is known to have beneficial effect, and can be achieved by transfer of NOS variant polynucleotides in vivo to target tissue.

NOS variant polynucleotides may be used to reduce the restenotic response after angioplasty or related interventional procedures, or to enhance the vasodilation response in the treatment of angina. Post interventional vascular therapy may be achieved via intraluminal administration of the NOS variant pharmaceuticals (e.g. a balloon-tipped catheter) or, for example, via a stent. (See, for example, Chapman, Cir. Res. 71:27–33 (1992); Restenosis Summit V, E. G. Topol Ed., Cleveland Clinic Heart Center (1993).)

The effects of nitric oxide on neural conduction and action potentials may also be exploited through administration of NOS variant polynucleotides to treat neurological disorders associated with low levels of nitric oxide.

NOS variant polynucleotides may be used in anti-cancer therapy to promote cancer cell death. High levels of NO are known to have cytotoxic and growth inhibiting effects. Furthermore, NO reacts with superoxide and other oxygen free radicals to produce highly toxic radicals such as peroxynitrite. In conjunction with radiotherapy, which induces the formation of oxygen free radicals as an aspect of its therapeutic effect, expression of NOS to increase NO production may permit the use of significantly lower radiation doses.

NOS variant polynucleotides may be used to inhibit the development or onset of premature labor. Nitric oxide is known to be directly involved in maintaining uterus relaxation during pregnancy. When the endogenous levels or availability of NO decrease, the uterus responds with increased contractility resulting in labor. Decreased levels of NO are known to contribute to the onset of preterm labor. By enhancing NO production in the uterus of a pregnant human or veterinary patient, the preterm contractions can be inhibited, and the preterm labor stopped before resulting in preterm delivery.

NOS variant polynucleotides that are administered to achieve or augment NO synthesis are preferably derived from the wild-type NOS of the same or related species as the one to which the polynucleotide is administered. In addition to the polynucleotide which encodes the NOS variant protein or polynucleotide, the construct further comprises a promoter which drives expression of the NOS variant in the cells of the targeted tissue. The particular promoter will be selected based on factors such as target tissue and desired expression controls. Delivery of the NOS variant polynucleotide into a patient may be either direct, in which case the patient is directly exposed to the nucleic acid or nucleic acid-carrying vector, or indirect, in which case cells are first transformed with the nucleic acid in vitro, then transplanted into the patient.

A retroviral vector may be used to deliver NOS variant polynucleotides (see Miller et al., 1993, Meth. Enzymol. 217:581–599). Retroviral vectors have been modified to delete retroviral sequences that are not necessary for packaging of the viral genome and are maintained in infected cells by integration into genomic sites upon cell division. More detail about retroviral vectors can be found in Boesen et al. (1994) *Biotherapy* 6:291–302, : Clowes et al. (1994) *J. Clin. Invest.* 93:644–651; Kiem et al. (1994) *Blood* 83:1467–1473; Salmons and Gunzberg (1993) *Human Gene Therapy* 4:129–141; and Grossman and Wilson (1993) *Curr. Opin. in Genetics and Devel.* 3:110–114.

Adenoviruses are other viral vectors that may be used to deliver NOS variant polynucleotides in vivo. Potential targets for adenovirus-based delivery systems include the respiratory epithelia, liver, the vasculature, the central nervous system, endothelial cells, and muscle. Adenoviruses have the advantage of being capable of infecting non-dividing cells. Kozarsky and Wilson present a review of adenovirus-based gene therapy. (See Kozarsky and Wilson (1993)

*Current Opinion in Genetics and Development* 3:499–503: Generally the multiplicity of infection of the adenovirus vectors will be in the range of about 1 to 100, preferably in the range of about 1 to 10. Instances of the use of adenoviruses in gene therapy can be found in Bout et al. (1994) *Human Gene Therapy* 5:3–10; Rosenfeld et al. (1991) *Science* 252:431–434; Rosenfeld et al. (1992) *Cell* 68:143–155; and Mastrangeli et al. (1993) *J. Clin. Invest.* 91:225–234. Advantageously, expression of the NOS variants described herein should allow one to achieve therapeutic effects at a lower multiplicity of infection. Thud the multiplicity of infection is not critical to the present invention.

Adeno-associated virus (AAV) has also been proposed for use in delivery of polynucleotides in vivo. ( See Walsh et al. (1993) *Proc. Soc. Exp. Biol. Med.* 204:289–300.) Herpes viruses are other viruses that can also be used.

As an alternative method of polynucleotide delivery in vivo, vectors containing NOS variant polynucleotide may be purified and injected directly into a target tissue. Similar approaches have been used successfully by others to express, for example, exogenous genes in rodent cardiac and skeletal muscle.

Liposomes may be employed to deliver vectors of the present invention to target tissues using methods known in the art. The liposomes may be constructed to contain a targeting moiety or ligand, such as an antigen, an antibody, or a virus on their surface to facilitate delivery to the appropriate tissue. For example, liposomes prepared with ultraviolet (UV) inactivated Hemagglutinating Virus of Japan (HVJ) may be used to deliver DNA to selected tissues (Morishita, et al.). The liposomes may also be surface-coated with phospholipid—polyethyleneglycol conjugates, to extend blood circulation time and allow for greater targeting via the bloodstream. Liposomes of this type are well known.

Receptor-mediated endocytic pathways for the uptake of DNA may permit the targeted delivery of NOS variant polynucleotides to specific cell types in vivo. Receptor-mediated methods of polynucleotide delivery in vivo involve the generation of complexes between vectors and specific polypeptide ligands that can be recognized by receptors on the cell surface.

For general reviews of the methods of in vivo polynucleotide delivery (also referred to as gene therapy), see Goldspiel et al (1993) *Clinical Pharmacy* 12:488–505; Wu and Wu (1991) *Biotherapy* 3:87–95; Tolstoshev (1993) *Ann. Rev. Pharmacol. Toxicol.* 32:573–596; Mulligan, (1993) *Science* 260:926–932; and Morgan and Anderson (1993) *Ann. Rev. Biochem.* 62:191–217; May, 1993, TIBTECH 11(5):155–215. Methods commonly known in the art of recombinant DNA technology which can be used are described in Ausubel et al. (eds.) (1993) *Current Protocols in Molecular Biology*, John Wiley & Sons, NY; and Kriegler (1990) *Gene Transfer and Expression*, A Laboratory Manual, Stockton Press, NY.

NOS Variant Proteins and Polypeptides.

The present invention also relates to NOS variant proteins and polypeptides, which may be used to increase production of NO in cells. Such variants are administered to cells in vitro or in vivo in the form of a liposome in which the NOS variant protein or polypeptide is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art.

EXAMPLES

The present invention will be described in greater detail with the aid of the following examples which should be considered as illustrative and non-limiting. All references cited herein are specifically incorporated by reference.

Example 1

Rat nNOS Trp 409 Variants

The targeted tryptophan residue in rat nNOS is at position 409 of the wild-type amino acid sequence. Variants comprising a phenylalanine (F) or tyrosine (Y) at position 409 in the amino acid sequence, referred to hereinafter as W409F and W409Y, were prepared using site-directed mutagenesis. Wild-type nNOS and mutants containing a $His_6$ tag attached to their N terminus were overexpressed in *Escherichia coli* strain BL21 (DE3) using a modified pCWori vector and were purified as described (Wu, et. al. (1996), *Biochem. Biophys. Res. Commun.* 22:439–444; Gachhui, (1998) *J. Biol. Chem.* 268:20037–20045) Adak, et al., *J. Biol. Chem.*, 1999. Restriction digestions, cloning, and bacterial growth were performed using standard procedures (Sambrook, J. et al (1989) *Molecular Cloning A Laboratory Manual*, Cold Spring Harbor Press, Plainview, N.Y. and Ausubel, F. M. et al. (1989) *Current Protocols in Molecular Biology*, John Wiley & Sons, New York, N.Y.). Transformations were done using a TransformAid kit from MBI Fermentas. DNA fragments were isolated using the AgarACE enzyme protocol from Promega. Site-directed mutagenesis was done using the Quick Change polymerase chain reaction in vitro mutagenesis kit from Stratagene. Incorporated mutations were confirmed by DNA sequencing. DNAs containing the desired mutations were transformed into *E. coli* for protein expression.

Oligonucleotides used to construct site-directed mutants in nNOS were synthesized by Life Technologies, Inc., or by Integrated DNA Technologies. Silent mutations coding for restriction sites were incorporated into the oligonucleotides to aid in screening. Mutations (bold), silent restriction sites (underlined), and their corresponding oligonucleotides were as follows:

W409F-NheI-sense: GCATGCCTTCCGGAAC GCTAGCCGATGTGTGGGCAG (SEQ. ID. NO. 6);

W409F-antisense: CTGCCCACACATCGGCTAGCGT-TCCGGAAGGCATGC (SEQ, ID. NO. 7);

409YNheI-sense: GCATGCCTACCGGAAC GCTAGCCGATGTGTGGGCAG (SEQ, ID. NO. 8); and

W409Y-antisense: CTGCCCACACATCGGCTAGCGT-TCCGGTAGGCATGC (SEQ, ID. NO. 9).

Characterization of Variants W409F and W409Y
A. UV-visible Spectra

Wild-type and mutant nNOS were expressed in *E. coli* and purified as described previously (Wu, et. al. (1996), *Biochem. Biophys. Res. Commun.* 22:439–444; Gachhui, (1998) *J. Biol. Chem.* 268:20037–20045). UV-visible spectra was recorded on a Hitachi U3110 Spectrophotometer in the absence or presence of 20 µM $H_4B$ and 1 mM Arg. The ferrous-CO adduct absorbing at 444 nm was used to quantitate the heme protein content using as extinction coefficient of 74 $mM^{-1} cm^{-1}$ (A444–A500). The optical spectrum of the W409F and W409Y mutants closely resembled that of wild-type nNOS at pH 7.6 in the absence of $H_4B$ and Arg. Addition of 20 $\mu$M $H_4B$ and 1 mM arginine to either mutant caused a spectral shift from low spin to high spin, indicating that these molecules bound. Dithionite reduction in the presence of Arg, $H_4B$, and CO produced a 444-nm absorbance peak for the ferrous-CO complex in both cases, indicating that their heme iron ligation is the same as in wild-type nNOS. Arg binding affinities were determined by spectral perturbation in the presence of 10 mM imidazole and 20 $\mu$M $H_4B$ (da Arg completely displaced bound imidazole during the titrations, and the Arg $K_s$ values for W409F and W409Y were 60 and 68 $\mu$M, respectively, compared with 55 $\mu$M for wild-type nNOS. Thus, Arg and $H_4B$ binding were not significantly perturbed by the mutation of Trp-409 to Tyr or Phe.

B. NO Synthesis, NADPH Oxidation, Cytochrome c Reduction, and $H_2O_2$-dependent nNOS Oxidation of NOHA.

The initial rate of NO synthesis, NADPH oxidation, or cytochrome c reduction by wild type and mutants was quantitated at 25° C. as described in Abu-Soud et al. (1997) J. Biol. Chem 272: 10769–10772. $H_2O_2$-dependent nNOS oxidation of NOHA to nitrite was assayed in 96-well microplates at 30° C. The assay volume was 100 $\mu$l and contained 40 mM EPPS, pH 7.6, 250 nM nNOS or mutants, 1 mM NOHA, 1 mM DTT, 25 units/ml superoxide dismutase 0.5 mM EDTA, and 4 $\mu$M $H_4B$. Reactions were initiated by adding 30 mM $H_2O_2$ and stopped after 10 min by adding 1300 units of catalase. Nitrite was detected at 550 nm using the Griess reagent (100 $\mu$L) and quantitated based on nitrite standards.

Table I compares the catalytic turnover numbers of wild-type nNOS and the Trp-409 mutants with regard to NO synthesis from Arg or NOHA, NADPH oxidation, and cytochrome c reduction in the presence or absence of $Ca^{2+}$/CaM.

TABLE I

Comparative analysis of catalytic activities of wild type nNOS and mutants
The turn over number ($k_{cat}$) is expressed as mol of product formed/mol of protein/min. NO synthesis from Arg and NOHA, NADPH oxidation, and cytochrome c reduction rates were determined at 25° C. as described under "Experimental Procedures." The values represent the mean and standard error for three measurements each.

| Activity | NNOS +CaM | NNOS -CaM | W409F +CaM | W409F -CaM | W409Y +CaM | W409Y -CaM |
|---|---|---|---|---|---|---|
| NO synthesis from Arg | 96 ± 5 | 0 | 286 ± 18 | 0 | 155 ± 15 | 0 |
| NO synthesis from NOHA | 115 ± 5 | 0 | 453 ± 11 | 0 | 180 ± 12 | 0 |
| NADPH oxidation | 170 ± 10 | 11.2 | 445 ± 20 | 5.6 | 237 ± 5 | 11.2 |
| Cytochrome c reduction | 7000 ± 220 | 500 ± 50 | 5000 ± 200 | 230 ± 20 | 5546 ± 300 | 280 ± 20 |

As shown in Table I above, substitution of Trp-409 with Phe or Tyr altered rates of NO synthesis and NADPH oxidation but did not alter cytochrome c reduction in any case, suggesting the mutations only affect the oxygenase domain of nNOS. Surprisingly, the W409F and W409Y mutants had 3- and 1.8-fold faster-rates of NO synthesis from Arg compared with the wild type, respectively. Corresponding rates of NADPH oxidation were increased, indicating a proportional increase in electron flux through the enzyme. The calculated NADPH stoichiometries were 1.7, 1.6, and 1.5 mol of NADPH oxidized/mol of NO generated from Arg for wild-type nNOS, W409F, and W409Y, respectively. These values are close to the theoretical minimum of 1.5 and therefore indicate tight coupling between NADPH oxidation and NO synthesis by the mutants. When NOHA replaced Arg as the substrate, an even greater hyperactivity was observed for both mutants (Table I).

To understand how the mutations increased rates of NO synthesis by nNOS, we first examined mutant activities in the $H_2O_2$-supported NOHA oxidation assay. This measures nitrite formation and is useful because the reaction does not require electrons from the reductase domain and does not result in formation of a heme-NO complex. Initial rates of nitrite formation by the mutant proteins were equivalent to wild-type nNOS. This suggests that the mutations increase NO synthesis in the NADPH-supported reaction by changing the rate of electron flux and/or the dynamics of heme-NO complex formation.

To examine how the mutations effect electron flux through nNOS, we compared their NADPH oxidation rates under a number of different conditions (Table II).

TABLE II

Effect of $H_4B$, Arg, and Arg analogs on NADPH oxidation by CaM-bound nNOS and mutant proteins
The turn over number ($k_{cat}$) is expressed in mol of NADPH oxidized/mol of protein/min. The rate of NADPH oxidation was measured at 25° C. The values represent the mean and standard error for three measurements each. NAME, nitro-L-arginine methyl ester.

| System | nNOS min$^{-1}$ | W409F min$^{-1}$ | W409Y min$^{-1}$ |
|---|---|---|---|
| $-H_4B$, $-Arg$ | 290 + 25 | 105 + 10 | 74 + 8 |
| $+H_4B$, $-Arg$ | 500 + 25 | 189 + 15 | 124 + 4 |
| $+H_4B$, NAME | 22 + 4 | 16 + 3 | 25 + 4 |
| $+H_4B$, Arg | 160 + 12 | 480 + 20 | 250 + 20 |
| $+H_4B$, agmatine | 250 + 20 | 180 + 10 | 170 + 10 |

CaM-bound, wild-type nNOS had a relatively high rate of NADPH oxidation in the absence of $H_4B$ and Arg, and this rate was increased approximately two times when $H_4B$ bound. NADPH oxidation rates for the CaM-bound Trp-409 mutants were slower is the absence of Arg and $H_4B$ but increased proportionally as for the wild-type in response to $H_4B$ (~2x). Addition of the heme reduction inhibitor nitro-L-Arg methyl ester to the $H_4B$-bound proteins decreased their NADPH oxidation rates to a level seen for the nNOS reductase domain alone, indicating that any additional NADPH oxidation above this value was associated with heme reduction. Together, these data indicate that electron flux through the heme is actually slower in the two mutants than in wild-type nNOS in the absence of NO synthesis. The addition of Arg to the CaM-bound, $H_4B$-saturated enzymes initiated NO synthesis in all cases and lowered the rate of NADPH oxidation in wild-type nNOS, as reported. In contrast, the Arg addition increased NADPH oxidation rates in both $H_4B$-bound mutants. To test if NO was involved in modulating the Arg effects, we utilized agmatine, a substrate analog that binds to nNOS without supporting NO synthesis. Agmatine decreased NADPH oxidation by wild-type nNOS compared with $H_4B$ alone but to a lesser extent than seen with Arg. For the mutants agmatine either did not effect the NADPH oxidation rate (W409F) or only increased it slightly (W409Y). These data show that electron flux through the heme is actually slower in the mutants under all conditions except when NO synthesis is taking place. This suggests that mutant hyperactivity and associated increase in electron flux must arise from a difference in NO interaction with the enzyme.

C. Ferrous-Nitrosyl Complex Formation During Steady State

NO down-regulates the rate of NO synthesis and associated electron flux by binding to the nNOS heme. We therefore investigated if NO binding to the heme was altered by the Trp-409 mutations during aerobic steady-state catalysis. In this study, 0.6 $\mu$M nNOS was diluted is an air-saturated 40 mM EPPS buffer, pH 7.6, containing 0.9 mM EDTA, 3 $\mu$M CaM, 200 $\mu$M DTT, 20 $\mu$M H$_4$B, 80 $\mu$M NADPH, and 1 mM Arg; final volume 1 ml. Reactions were started by adding 1.2 mM Ca$^{2+}$ and monitored by wavelength scanning at 15° C. For wild-type nNOS, a significant percentage accumulated as the 6-coordinate ferrous-NO complex during the steady-state, as judged by the buildup of characteristic absorbance peaks at 436 and 560 nm. Under the same conditions, the Trp-409 mutants had either a small (W409F) or no (W409Y) detectable absorbance buildup at 436 nm, indicating their 6-coordinate NO complexes did not accumulate during steady-state NO synthesis.

D. Ferric- and Ferrous-NO Complex Formation Under Anaerobic Conditions

Given the above, we investigated if either mutant could form stable ferric or ferrous NO complexes with authentic NO under an anaerobic atmosphere in the presence of Arg and H$_4$B, as occurs for wild-type nNOS. Concentrated small amounts of nNOS or mutants were placed into an anaerobic cuvette with 4 $\mu$M H$_4$B, 1 mM Arg, and 200 $\mu$M DTT and made anaerobic by repeated cycles of evacuation and equilibration with deoxygenated argon gas. A 40 mM EPPS buffer containing 4 $\mu$M H$_4$B, 1 mM Arg, and 200 $\mu$M DTT was separately made anaerobic, and 1 ml of this solution was transferred to the cuvette. NO gas was added to the head space and dissolved by mixing. Dithionite solution was then added in some cases.

Figure 3:
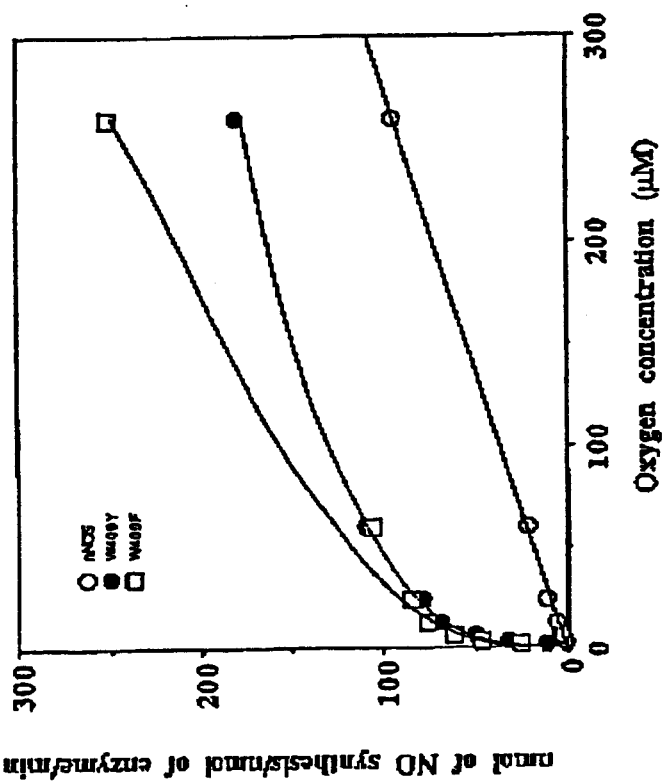
FIG. 3 shows the effect of $O_2$ levels on activity of the non-variant and variant nNOS.

Wild-type nNOS and both mutants all formed stable 6-coordinate ferric NO complexes that display a Soret peak at 440 mn and visible peaks at 549 and 580 nm. A small amount of dithionite was then added to reduce each enzyme. This formed a stable 6-coordinate ferrous-NO complex in wild-type nNOS but generated unstable ferrous-NO complexes in both mutants. We conclude that the W409 mutations destabilize the ferrous-NO complex that normally accumulates during NO synthesis by nNOS E. Enzymatic Activity of NOS Variants at Physiological Levels of O$_2$ The effect of O$_2$ concentration on activity of a variant nNOS polypeptide was demonstrated using reaction mixtures that contained concentrated nNOS (40 nM), placed in septum-sealed cuvettes and mixed with various ratios of N$_2$ or air saturated buffer that contained 40 mM EPPS, 150 $\mu$M/ml calmodulin, 0.62 mM Calcium chloride, 0.3 mM DTT, 5 mM Arg, 4 $\mu$M each of H4B, FAD, and FMN, 100 units/ml catalase, 10 units/ml super oxide dismutase, and 10 $\mu$M oxyhemoglobin. The reaction was started by adding 0.2 mM NADPH. Rates of synthesis were quantified as follows: the initial rate of NO synthesis by nNOS was quantitated at 25° C. using oxyhemoglobin assay for NO, according to the method found in Abu-Soud and Stuehr (1993) *Proc. Natl. Acad. Sci. U.S.A.* 90:10769–10772. The NO mediated conversion of oxyhemoglobin to met-hemoglobin was monitored over time as an absorbence increase at 401 nm, and quantitated using the extinction coefficient of 38 mM$^{-1}$ cm$^{-1}$. Quantitation was done with a Hitachi U2000 spectrophotometer. O$_2$ concentration measurement in each reaction was calculated based on the O$_2$ concentration of a saturated buffer at 25° C. (approximately 0.26 mM) and the mixing ratios of this solution with an anaerobic buffer that contained no oxygen. As shown in FIG. 3, W409F and W409Y produce NO at rates that are faster than the wild-type nNOS protein at O$_2$ levels ranging from 0 to 230 mm O$_2$. The difference in the enzymatic activity of the NOS variant and wild-type NOS is most pronounced at low concentrations of O$_2$, i.e., concentrations ranging from 0 to 50 $\mu$M.

Example 2

Human nNOS Variant

Human nNOS has the amino acid sequence set forth in SEQ ID NO:1. A variant of human nNOS is prepared by substituting the tryptophan at position 414 in this sequence with a tyrosine or phenylalanine using the procedures described above in Example 1.

Example 3

Human eNOS Variant

Human eNOS has the amino acid sequence set forth in SEQ ID NO:3. A variant of human eNOS is prepared by substituting the tryptophan at position 178 in this sequence with a phenylalanine or tyrosine using the procedures described above in Example 1.

Example 4

Human iNOS Variant

Human iNOS has the amino acid sequence set forth in SEQ ID NO:1. A variant of human iNOS is prepared by substituting the tryptophan at position 194 in this sequence with a phenylalanine or tyrosine using the procedures described above in Example 1.

Example 5

Cells Transfected With a Polynucleotide Encoding a NOS Variant

R293 cells are transfected with a plasmid comprising a polynucleotide encoding W409F and a neomycin resistance gene using a commercially available lipofectamine transforming reagent. The R293 cells are then cultured at low density in the presence of neomycin to select for stable transfectant cell lines. Several cells lines are then screened for levels of expression of NOS variant polypeptides by growing about 100 million cells of each candidate and then making a soluble cell lysate from these cells, which is then assayed for NO synthesis activity using standard cell-lysate assay as described above in example 1. The cell line exhibiting the highest NO synthesis activity per mg of soluble protein is then used to evaluate NO synthesis versus O$_2$ concentration measurements. Such cell line may also be used to study the effect of elevated levels of intracellular NO on cellular processes.

The invention now being fully described, it will be apparent to one of ordinary skill in the art that many changes and modifications can be made thereto without departing from the spirit or scope of the appended claims.

What is claimed is:

1. An isolated polynucleotide encoding a variant of a corresponding wild-type nitric oxide synthase, wherein the corresponding wild-type nitric oxide synthase comprises an oxygenase domain having a cysteine residue that binds heme, an alpha three helix, and a tryptohan residue that is located on the alpha 3 helix, six residues upstream from the cysteine residue that binds heme, a reductase domain having an NADPH binding site, and a calmodulin binding region;

wherein said variant is a substitution mutant of the corresponding wild-type nitric oxide synthase in which the tryptophan residue that is located on the alpha 3 helix, six residues upstream from the cysteine that binds heme in the corresponding wild-type sequence is substituted with a tyrosine or phenylalanine residue and in which 0 to 10% of the other amino acids in the corresponding wild-type nitric oxide synthase are substituted with conservative amino acids, and wherein said variant has an in vitro enzymatic activity that is greater than the in vitro enzymatic activity of the corresponding wild-type nitric oxide synthase.

2. An isolated polynucleotide encoding a variant of a corresponding wild-type endothelial nitric oxide synthase (eNOS), neuronal nitric oxide synthase (nNOS) or inducible nitric oxide synthase (iNOS), wherein the corresponding wild-type eNOS, nNOS, or iNOS comprises an oxygenase domain having a cysteine which binds heme, an alpha three helix, a tryptohan residue that is located on the alpha 3 helix, six residues upstream from the cysteine which binds heme, a reductase domain having an NADPH binding site, and a calmodulin binding region;

wherein the variant comprises:

(a) a first mutation in which the tryptophan residue that is located on the alpha 3 helix, six residues upstream from the cysteine which binds heme in the corresponding wild-type sequence is substituted with a phenylalanine or tyrosine residue, (b) a second mutation comprising one or a combination of mutations selected from the group consisting of, a substitution with an aspartic acid of a serine residue in the NADPH binding site of wild-type eNOS or nNOS, and a truncation or deletion of a leader sequence in the corresponding wild-type eNOS, nNOS, or iNOS, and (c) optionally, additionally substitution mutations of 5% or less of other amino acid residues in the corresponding wild-type eNOS, nNOS, or iNOS with conservative amino acid residues;

wherein the variant has an in vitro enzymatic activity that is greater than the in vitro enzymatic activity of the corresponding wild-type eNOS, nNOS, or iNOS.

3. The isolated polynucleotide of claim 2 wherein said variant is a polypeptide that lacks a portion or all of the leader sequence of the corresponding wild-type-nitric oxide synthase.

4. The isolated polynucleotide of claim 1 wherein said variant is a variant of a human inducible nitric oxide synthase.

5. The isolated polynucleotide of claim 1 wherein said variant is a variant of a human neuronal nitric oxide synthase.

6. The isolated polynucleotide of claim 1 wherein said variant is a variant of a human endothelial nitric oxide synthase.

7. The isolated polynucleotide of claim 1 wherein said variant comprises an amino acid sequence which is at least 95% identical to a full-length amino acid sequence of a corresponding wild-type human neuronal, endothelial or inducible nitric oxide synthase or a corresponding wild-type human neuronal, endothelial or inducible nitric oxide synthase that lacks a leader sequence.

8. A nucleic acid construct comprising a nucleotide sequence which encodes a variant of a corresponding wild-type nitric oxide synthase and a promoter operably linked to the encoding sequence of said variant, wherein the corresponding wild-type nitric oxide synthase comprises an oxygenase domain having a cysteine which binds heme, an alpha three helix, and a tryptohan residue that is located on the alpha 3 helix, six residues upstream from the cysteine which binds heme, a reductase domain having an NADPH binding site, and a calmodulin binding region, wherein said variant is a substitution mutant of the corresponding wild-type nitric oxide synthase in which the tryptophan residue that is located on the alpha 3 helix, six residues upstream from the cysteine which binds heme in the wild-type sequence is substituted with a tyrosine or phenylalanine residue and in which 10% or less of amino acid residues in the corresponding wild-type nitric oxide syntase are substituted with conservative amino acid residues, and wherein said variant has an in vitro enzymatic activity that is greater than the in vitro enzymatic activity of a corresponding nitric oxide synthase whose alpha 3 helix has a tryptophan residue six residues upstream from the cysteine which binds heme.

9. The nucleic acid construct of claim 8 wherein said construct further comprises a nucleotide sequence which encodes GTP cyclohydrolase.

10. A transformed cell which comprises the construct of claim 8, wherein said transformed cell expresses the nitric oxide synthase variant.

11. The polynucleotide of claim 2 wherein the variant is a variant of a human inducible nitric oxide synthase.

12. The polynucleotide of claim 2 wherein the variant is a variant of a human neuronal nitric oxide synthase.

13. The polynucleotide of claim 2 wherein the variant is a variant of a human endothelial nitric oxide synthase.

14. An isolated polynucleotide encoding a variant of a corresponding wild-type endothelial nitric oxide synthase (eNOS) or neuronal nitric oxide synthase (nNOS), wherein the corresponding wild-type eNOS or nNOS comprises an oxygenase domain having a cysteine which binds heme, an alpha three helix, a tryptohan residue that is located on the alpha 3 helix, six residues upstream from the cysteine which binds heme, a reductase domain having an NADPH binding site, and a calmodulin binding region;

wherein the variant comprises:
(a) a first mutation in which the tryptophan residue that is located on the alpha 3 helix, six residues upstream from the cysteine which binds heme in the corresponding wild-type sequence is substituted with a phenylalanine or tyrosine residue,
(b) a second mutation comprising one or a combination of mutations selected from the group consisting of a replacement of amino acid residues in the wild-type eNOS or nNOS calmodulin binding region with amino acid residues specific for the wild-type calmodulin binding sequence of an inducible nitric oxide synthase, a substitution with an aspartic acid of a serine residue in the NADPH binding site of the corresponding wild-type eNOS or nNOS, and a truncation or deletion of a leader sequence in the corresponding wild-type eNOS, or nNOS, and
(c) optionally, additional substitution mutations of 5% or less of other amino acid residues in the corresponding wild-type eNOS, or nNOS, with conservative amino acid residues; wherein the variant has an in vitro enzymatic activity that is greater than the in vitro enzymatic activity of the corresponding wild-type eNOS, or nNOS.

15. An isolated polynucleotide encoding a variant of a corresponding wild-type endothelial nitric oxide synthase (eNOS) or neuronal nitric oxide synthase (nNOS), wherein the corresponding wild-type eNOS or nNOS comprises an oxygenase domain having a cysteine which binds heme, an alpha three helix, a tryptohan residue that is located on the alpha 3 helix, six residues upstream from the cysteine which binds heme, a reductase domain having an NADPH binding site, and a calmodulin binding region;

wherein the variant comprises:
(a) a first mutation in which the tryptophan residue that is located on the alpha 3 helix, six residues upstream from the cysteine which binds heme in the corresponding wild-type sequence is substituted with a phenylalanine or tyrosine residue,
(b) a second mutation comprising one or a combination of mutations selected from the group consisting of a deletion of an auto-inhibitory loop in the reductase domain of the corresponding wild type e-NOS or nNOS, a substitution with an aspartic acid of a serine residue in the NADPH binding site of the corresponding wild-type eNOS or nNOS, and a truncation or deletion of a leader sequence in the corresponding wild-type eNOS, or nNOS, and
(c) optionally, additional substitution mutations of 5% or less of other amino acid residues in the corresponding wild-type eNOS, or nNOS, with conservative amino acid residues; wherein the variant has an in vitro enzymatic activity that is greater than the in vitro enzymatic activity of the corresponding wild-type eNOS, or nNOS.

16. An isolated polynucleotide encoding a variant of a corresponding wild-type endothelial nitric oxide synthase (eNOS), neuronal nitric oxide synthase (nNOS) or inducible nitric oxide synthase *iNOS),* wherein the corresponding wild-type eNOS, nNOS, or iNOS comprises an oxygenase domain having a cysteine which binds heme, an alpha three helix, a tryptohan residue that is located on the alpha 3 helix, six residues upstream from the cysteine which binds heme, a reductase domain having an NADPH binding site, and a calmodulin binding region;

wherein the variant comprises:
  (a) a first mutation in which the tryptophan residue that is located on the alpha 3 helix, six residues upstream from the cysteine which binds heme in the corresponding wild-type sequence is substituted with a phenylalanine or tyrosine residue,
  (b) a second mutation comprising one or a combination of mutations selected from the group consisting of a mutation which renders the variant of the corresponding wild-type eNOS or nNOS calcium independent—with—(b) a second mutation comprising one or a combination of mutations selected from the group consisting of a deletion of an autoinhibitory loop in the reductase domain of the corresponding wild type eNOS or nNOS, a replacement of the amino acid residues in the wild-type eNOS or nNOS calmodulin binding region with amino acid residues specific for the wild-type calmodulin binding sequence of an inducible nitric oxide synthase,
  (c) optionally, additional substitution mutations of 5% or less of other amino acid residues in the corresponding wild-type eNOS, nNOS, or iNOS with conservative amino acid residues;

wherein the variant has an in vitro enzymatic activity that is greater than the in vitro enzymatic activity of the corresponding wild-type eNOS, nNOS, or iNOS.

\* \* \* \* \*

UNITED STATES PATENT AND TRADEMARK OFFICE
CERTIFICATE OF CORRECTION

PATENT NO.   : 6,620,616 B1
DATED        : September 16, 2003
INVENTOR(S)  : Dennis J. Stuehr and Subrata Adak It is certified that error appears in the above-identified patent and that said Letters Patent is hereby corrected as shown below:

Column 48,
Line 60, after "of," please delete ",".
Line 66, after "optionally," please delete "additionally" and insert -- additional --.

Column 50,
Line 65, after "synthase" please delete "*iNOS)*" and insert -- (iNOS) --.

Column 51,
Line 12, please delete "(b) a second mutation comprising one or a combination of mutations selected from the group consisting of a mutation which renders the variant of the corresponding wild-type eNOS or nNOS calcium independent - with -"

Signed and Sealed this

Twenty-seventh Day of April, 2004

JON W. DUDAS
*Acting Director of the United States Patent and Trademark Office*

SEQUENCE LISTING

<160> NUMBER OF SEQ ID NOS: 9

<210> SEQ ID NO 1
<211> LENGTH: 1434
<212> TYPE: PRT
<213> ORGANISM: Homo sapiens

<400> SEQUENCE: 1

```
Met Glu Asp His Met Phe Gly Val Gln Gln Ile Gln Pro Asn Val Ile
1               5                   10                  15

Ser Val Arg Leu Phe Lys Arg Lys Val Gly Gly Leu Gly Phe Leu Val
            20                  25                  30

Lys Glu Arg Val Ser Lys Pro Pro Val Ile Ile Ser Asp Leu Ile Arg
        35                  40                  45

Gly Gly Ala Ala Glu Gln Ser Gly Leu Ile Gln Ala Gly Asp Ile Ile
    50                  55                  60

Leu Ala Val Asn Gly Arg Pro Leu Val Asp Leu Ser Tyr Asp Ser Ala
65                  70                  75                  80

Leu Glu Val Leu Arg Gly Ile Ala Ser Glu Thr His Val Val Leu Ile
            85                  90                  95

Leu Arg Gly Pro Glu Gly Phe Thr Thr His Leu Glu Thr Thr Phe Thr
            100                 105                 110

Gly Asp Gly Thr Pro Lys Thr Ile Arg Val Thr Gln Pro Leu Gly Pro
        115                 120                 125

Pro Thr Lys Ala Val Asp Leu Ser His Gln Pro Pro Ala Gly Lys Glu
    130                 135                 140

Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
            165                 170                 175

Gly Leu Ala Pro Arg Pro Pro Gly Gln Asp Pro Ala Lys Lys Ala Thr
            180                 185                 190

Arg Val Ser Leu Gln Gly Arg Gly Glu Asn Asn Glu Leu Leu Lys Glu
        195                 200                 205

Ile Glu Pro Val Leu Ser Leu Leu Thr Ser Gly Ser Arg Gly Val Lys
    210                 215                 220

Gly Gly Ala Pro Ala Lys Ala Glu Met Lys Asp Met Gly Ile Gln Val
225                 230                 235                 240

Asp Arg Asp Leu Asp Gly Lys Ser His Lys Pro Leu Pro Leu Gly Val
            245                 250                 255

Glu Asn Asp Arg Val Phe Asn Asp Leu Trp Gly Lys Gly Asn Val Pro
            260                 265                 270

Val Val Leu Asn Asn Pro Tyr Ser Glu Lys Glu Gln Pro Pro Thr Ser
        275                 280                 285

Gly Lys Gln Ser Pro Thr Lys Asn Gly Ser Pro Ser Lys Cys Pro Arg
    290                 295                 300

Phe Leu Lys Val Lys Asn Trp Glu Thr Glu Val Val Leu Thr Asp Thr
305                 310                 315                 320

Leu His Leu Lys Ser Thr Leu Glu Thr Gly Cys Thr Glu Tyr Ile Cys
            325                 330                 335

Met Gly Ser Ile Met His Pro Ser Gln His Ala Arg Arg Pro Glu Asp
            340                 345                 350

Val Arg Thr Lys Gly Gln Leu Phe Pro Leu Ala Lys Glu Phe Ile Asp
```

-continued

```
            355                 360                 365
Gln Tyr Tyr Ser Ser Ile Lys Arg Phe Gly Ser Lys Ala His Met Glu
        370                 375                 380

Arg Leu Glu Glu Val Asn Lys Glu Ile Asp Thr Thr Ser Thr Tyr Gln
385                 390                 395                 400

Leu Lys Asp Thr Glu Leu Ile Tyr Gly Ala Lys His Ala Trp Arg Asn
                405                 410                 415

Ala Ser Arg Cys Val Gly Arg Ile Gln Trp Ser Lys Leu Gln Val Phe
                420                 425                 430

Asp Ala Arg Asp Cys Thr Thr Ala His Gly Met Phe Asn Tyr Ile Cys
            435                 440                 445

Asn His Val Lys Tyr Ala Thr Asn Lys Gly Asn Leu Arg Ser Ala Ile
    450                 455                 460

Thr Ile Phe Pro Gln Arg Thr Asp Gly Lys His Asp Phe Arg Val Trp
465                 470                 475                 480

Asn Ser Gln Leu Ile Arg Tyr Ala Gly Tyr Lys Gln Pro Asp Gly Ser
                485                 490                 495

Thr Leu Gly Asp Pro Ala Asn Val Gln Phe Thr Glu Ile Cys Ile Gln
            500                 505                 510

Gln Gly Trp Lys Pro Pro Arg Gly Arg Phe Asp Val Leu Pro Leu Leu
    515                 520                 525

Leu Gln Ala Asn Gly Asn Asp Pro Glu Leu Phe Gln Ile Pro Pro Glu
530                 535                 540

Leu Val Leu Glu Val Pro Ile Arg His Pro Lys Phe Glu Trp Phe Lys
545                 550                 555                 560

Asp Leu Gly Leu Lys Trp Tyr Gly Leu Pro Ala Val Ser Asn Met Leu
                565                 570                 575

Leu Glu Ile Gly Gly Leu Glu Phe Ser Ala Cys Pro Phe Ser Gly Trp
            580                 585                 590

Tyr Met Gly Thr Glu Ile Gly Val Arg Asp Tyr Cys Asp Asn Ser Arg
        595                 600                 605

Tyr Asn Ile Leu Glu Glu Val Ala Lys Lys Met Asn Leu Asp Met Arg
    610                 615                 620

Lys Thr Ser Ser Leu Trp Lys Asp Gln Ala Leu Val Glu Ile Asn Ile
625                 630                 635                 640

Ala Val Leu Tyr Ser Phe Gln Ser Asp Lys Val Thr Ile Val Asp His
                645                 650                 655

His Ser Ala Thr Glu Ser Phe Ile Lys His Met Glu Asn Glu Tyr Arg
            660                 665                 670

Cys Arg Gly Gly Cys Pro Ala Asp Trp Val Trp Ile Val Pro Pro Met
        675                 680                 685

Ser Gly Ser Ile Thr Pro Val Phe His Gln Glu Met Leu Asn Tyr Arg
    690                 695                 700

Leu Thr Pro Ser Phe Glu Tyr Gln Pro Asp Pro Trp Asn Thr His Val
705                 710                 715                 720

Trp Lys Gly Thr Asn Gly Thr Pro Thr Lys Arg Arg Ala Ile Gly Phe
                725                 730                 735

Lys Lys Leu Ala Glu Ala Val Lys Phe Ser Ala Lys Leu Met Gly Gln
            740                 745                 750

Ala Met Ala Lys Arg Val Lys Ala Thr Ile Leu Tyr Ala Thr Glu Thr
        755                 760                 765

Gly Lys Ser Gln Ala Tyr Ala Lys Thr Leu Cys Glu Ile Phe Lys His
    770                 775                 780
```

-continued

```
Ala Phe Asp Ala Lys Val Met Ser Met Glu Glu Tyr Asp Ile Val His
785                 790                 795                 800

Leu Glu His Glu Thr Leu Val Leu Val Val Thr Ser Thr Phe Gly Asn
                805                 810                 815

Gly Asp Pro Pro Glu Asn Gly Glu Lys Phe Gly Cys Ala Leu Met Glu
            820                 825                 830

Met Arg His Pro Asn Ser Val Gln Glu Arg Lys Ser Tyr Lys Val
        835                 840                 845

Arg Phe Asn Ser Val Ser Tyr Ser Asp Ser Gln Lys Ser Ser Gly
    850                 855                 860

Asp Gly Pro Asp Leu Arg Asp Asn Phe Glu Ser Ala Gly Pro Leu Ala
865                 870                 875                 880

Asn Val Arg Phe Ser Val Phe Gly Leu Gly Ser Arg Ala Tyr Pro His
                885                 890                 895

Phe Cys Ala Phe Gly His Ala Val Asp Thr Leu Leu Glu Glu Leu Gly
                900                 905                 910

Gly Glu Arg Ile Leu Lys Met Arg Glu Gly Asp Glu Leu Cys Gly Gln
            915                 920                 925

Glu Glu Ala Phe Arg Thr Trp Ala Lys Val Phe Lys Ala Ala Cys
    930                 935                 940

Asp Val Phe Cys Val Gly Asp Asp Val Asn Ile Glu Lys Ala Asn Asn
945                 950                 955                 960

Ser Leu Ile Ser Asn Asp Arg Ser Trp Lys Arg Asn Lys Phe Arg Leu
                965                 970                 975

Thr Phe Val Ala Glu Ala Pro Glu Leu Thr Gln Gly Leu Ser Asn Val
            980                 985                 990

His Lys Lys Arg Val Ser Ala Ala  Arg Leu Leu Ser Arg  Gln Asn Leu
        995                 1000                1005

Gln Ser  Pro Lys Ser Ser Arg  Ser Thr Ile Phe Val  Arg Leu His
    1010                1015                1020

Thr Asn  Gly Ser Gln Glu Leu  Gln Tyr Gln Pro Gly  Asp His Leu
    1025                1030                1035

Gly Val  Phe Pro Gly Asn His  Glu Asp Leu Val Asn  Ala Leu Ile
    1040                1045                1050

Glu Arg  Leu Glu Asp Ala Pro  Pro Val Asn Gln Met  Val Lys Val
    1055                1060                1065

Glu Leu  Leu Glu Glu Arg Asn  Thr Ala Leu Gly Val  Ile Ser Asn
    1070                1075                1080

Trp Thr  Asp Glu Leu Arg Leu  Pro Pro Cys Thr Ile  Phe Gln Ala
    1085                1090                1095

Phe Lys  Tyr Tyr Leu Asp Ile  Thr Thr Pro Pro Thr  Pro Leu Gln
    1100                1105                1110

Leu Gln  Gln Phe Ala Ser Leu  Ala Thr Ser Glu Lys  Glu Lys Gln
    1115                1120                1125

Arg Leu  Leu Val Leu Ser Lys  Gly Leu Gln Glu Tyr  Glu Glu Trp
    1130                1135                1140

Lys Trp  Gly Lys Asn Pro Thr  Ile Val Glu Val Leu  Glu Glu Phe
    1145                1150                1155

Pro Ser  Ile Gln Met Pro Ala  Thr Leu Leu Leu Thr  Gln Leu Ser
    1160                1165                1170

Leu Leu  Gln Pro Arg Tyr Tyr  Ser Ile Ser Ser Ser  Pro Asp Met
    1175                1180                1185
```

```
Tyr Pro Asp Glu Val His Leu Thr Val Ala Ile Val Ser Tyr Arg
        1190            1195                1200

Thr Arg Asp Gly Glu Gly Pro Ile His His Gly Val Cys Ser Ser
        1205            1210                1215

Trp Leu Asn Arg Ile Gln Ala Asp Glu Leu Val Pro Cys Phe Val
        1220            1225                1230

Arg Gly Ala Pro Ser Phe His Leu Pro Arg Asn Pro Gln Val Pro
        1235            1240                1245

Cys Ile Leu Val Gly Pro Gly Thr Gly Ile Ala Pro Phe Arg Ser
        1250            1255                1260

Phe Trp Gln Gln Arg Gln Phe Asp Ile Gln His Lys Gly Met Asn
        1265            1270                1275

Pro Cys Pro Met Val Leu Val Phe Gly Cys Arg Gln Ser Lys Ile
        1280            1285                1290

Asp His Ile Tyr Arg Glu Glu Thr Leu Gln Ala Lys Asn Lys Gly
        1295            1300                1305

Val Phe Arg Glu Leu Tyr Thr Ala Tyr Ser Arg Glu Pro Asp Lys
        1310            1315                1320

Pro Lys Lys Tyr Val Gln Asp Ile Leu Gln Glu Gln Leu Ala Glu
        1325            1330                1335

Ser Val Tyr Arg Ala Leu Lys Glu Gln Gly Gly His Ile Tyr Val
        1340            1345                1350

Cys Gly Asp Val Thr Met Ala Ala Asp Val Leu Lys Ala Ile Gln
        1355            1360                1365

Arg Ile Met Thr Gln Gln Gly Lys Leu Ser Ala Glu Asp Ala Gly
        1370            1375                1380

Val Phe Ile Ser Arg Met Arg Asp Asp Asn Arg Tyr His Glu Asp
        1385            1390                1395

Ile Phe Gly Val Thr Leu Arg Thr Tyr Glu Val Thr Asn Arg Leu
        1400            1405                1410

Arg Ser Glu Ser Ile Ala Phe Ile Glu Glu Ser Lys Lys Asp Thr
        1415            1420                1425

Asp Glu Val Phe Ser Ser
        1430

<210> SEQ ID NO 2
<211> LENGTH: 1429
<212> TYPE: PRT
<213> ORGANISM: Rattus rattus

<400> SEQUENCE: 2

Met Glu Glu Asn Thr Phe Gly Val Gln Gln Ile Gln Pro Asn Val Ile
1               5                   10                  15

Ser Val Arg Leu Phe Lys Arg Lys Val Gly Gly Leu Gly Phe Leu Val
                20                  25                  30

Lys Glu Arg Val Ser Lys Pro Pro Val Ile Ile Ser Asp Leu Ile Arg
            35                  40                  45

Gly Gly Ala Ala Glu Gln Ser Gly Leu Ile Gln Ala Gly Asp Ile Ile
        50                  55                  60

Leu Ala Val Asn Asp Arg Pro Leu Val Asp Leu Ser Tyr Asp Ser Ala
65                  70                  75                  80

Leu Glu Val Leu Arg Gly Ile Ala Ser Glu Thr His Val Val Leu Ile
                85                  90                  95

Leu Arg Gly Pro Glu Gly Phe Thr Thr His Leu Glu Thr Thr Phe Thr
            100                 105                 110
```

-continued

```
Gly Asp Gly Thr Pro Lys Thr Ile Arg Val Thr Gln Pro Leu Gly Pro
            115                 120                 125
Pro Thr Lys Ala Val Asp Leu Ser His Gln Pro Ser Ala Ser Lys Asp
    130                 135                 140
Gln Ser Leu Ala Val Asp Arg Val Thr Gly Leu Gly Asn Gly Pro Gln
145                 150                 155                 160
His Ala Gln Gly His Gly Gln Gly Ala Gly Ser Val Ser Gln Ala Asn
                165                 170                 175
Gly Val Ala Ile Asp Pro Thr Met Lys Ser Thr Lys Ala Asn Leu Gln
            180                 185                 190
Asp Ile Gly Glu His Asp Glu Leu Leu Lys Glu Ile Glu Pro Val Leu
            195                 200                 205
Ser Ile Leu Asn Ser Gly Ser Lys Ala Thr Asn Arg Gly Gly Pro Ala
    210                 215                 220
Lys Ala Glu Met Lys Asp Thr Gly Ile Gln Val Asp Arg Asp Leu Asp
225                 230                 235                 240
Gly Lys Ser His Lys Ala Pro Pro Leu Gly Gly Asp Asn Asp Arg Val
                245                 250                 255
Phe Asn Asp Leu Trp Gly Lys Asp Asn Val Pro Val Ile Leu Asn Asn
            260                 265                 270
Pro Tyr Ser Glu Lys Glu Gln Ser Pro Thr Ser Gly Lys Gln Ser Pro
    275                 280                 285
Thr Lys Asn Gly Ser Pro Ser Arg Cys Pro Arg Phe Leu Lys Val Lys
    290                 295                 300
Asn Trp Glu Thr Asp Val Val Leu Thr Asp Thr Leu His Leu Lys Ser
305                 310                 315                 320
Thr Leu Glu Thr Gly Cys Thr Glu His Ile Cys Met Gly Ser Ile Met
                325                 330                 335
Leu Pro Ser Gln His Thr Arg Lys Pro Glu Asp Val Arg Thr Lys Asp
            340                 345                 350
Gln Leu Phe Pro Leu Ala Lys Glu Phe Leu Asp Gln Tyr Tyr Ser Ser
    355                 360                 365
Ile Lys Arg Phe Gly Ser Lys Ala His Met Asp Arg Leu Glu Glu Val
    370                 375                 380
Asn Lys Glu Ile Glu Ser Thr Ser Thr Tyr Gln Leu Lys Asp Thr Glu
385                 390                 395                 400
Leu Ile Tyr Gly Ala Lys His Ala Trp Arg Asn Ala Ser Arg Cys Val
                405                 410                 415
Gly Arg Ile Gln Trp Ser Lys Leu Gln Val Phe Asp Ala Arg Asp Cys
            420                 425                 430
Thr Thr Ala His Gly Met Phe Asn Tyr Ile Cys Asn His Val Lys Tyr
            435                 440                 445
Ala Thr Asn Lys Gly Asn Leu Arg Ser Ala Ile Thr Ile Phe Pro Gln
    450                 455                 460
Arg Thr Asp Gly Lys His Asp Phe Arg Val Trp Asn Ser Gln Leu Ile
465                 470                 475                 480
Arg Tyr Ala Gly Tyr Lys Gln Pro Asp Gly Ser Thr Leu Gly Asp Pro
                485                 490                 495
Ala Asn Val Gln Phe Thr Glu Ile Cys Ile Gln Gln Gly Trp Lys Ala
            500                 505                 510
Pro Arg Gly Arg Phe Asp Val Leu Pro Leu Leu Leu Gln Ala Asn Gly
            515                 520                 525
```

```
Asn Asp Pro Glu Leu Phe Gln Ile Pro Pro Glu Leu Val Leu Glu Val
530                 535                 540

Pro Ile Arg His Pro Lys Phe Asp Trp Phe Lys Asp Leu Gly Leu Lys
545                 550                 555                 560

Trp Tyr Gly Leu Pro Ala Val Ser Asn Met Leu Leu Glu Ile Gly Gly
                565                 570                 575

Leu Glu Phe Ser Ala Cys Pro Phe Ser Gly Trp Tyr Met Gly Thr Glu
                580                 585                 590

Ile Gly Val Arg Asp Tyr Cys Asp Asn Ser Arg Tyr Asn Ile Leu Glu
                595                 600                 605

Glu Val Ala Lys Lys Met Asp Leu Asp Met Arg Lys Thr Ser Ser Leu
610                 615                 620

Trp Lys Asp Gln Ala Leu Val Glu Ile Asn Ile Ala Val Leu Tyr Ser
625                 630                 635                 640

Phe Gln Ser Asp Lys Val Thr Ile Val Asp His His Ser Ala Thr Glu
                645                 650                 655

Ser Phe Ile Lys His Met Glu Asn Glu Tyr Arg Cys Arg Gly Gly Cys
                660                 665                 670

Pro Ala Asp Trp Val Trp Ile Val Pro Pro Met Ser Gly Ser Ile Thr
                675                 680                 685

Pro Val Phe His Gln Glu Met Leu Asn Tyr Arg Leu Thr Pro Ser Phe
                690                 695                 700

Glu Tyr Gln Pro Asp Pro Trp Asn Thr His Val Trp Lys Gly Thr Asn
705                 710                 715                 720

Gly Thr Pro Thr Lys Arg Arg Ala Ile Gly Phe Lys Lys Leu Ala Glu
                725                 730                 735

Ala Val Lys Phe Ser Ala Lys Leu Met Gly Gln Ala Met Ala Lys Arg
                740                 745                 750

Val Lys Ala Thr Ile Leu Tyr Ala Thr Glu Thr Gly Lys Ser Gln Ala
                755                 760                 765

Tyr Ala Lys Thr Leu Cys Glu Ile Phe Lys His Ala Phe Asp Ala Lys
                770                 775                 780

Ala Met Ser Met Glu Glu Tyr Asp Ile Val His Leu Glu His Glu Ala
785                 790                 795                 800

Leu Val Leu Val Val Thr Ser Thr Phe Gly Asn Gly Asp Pro Pro Glu
                805                 810                 815

Asn Gly Glu Lys Phe Gly Cys Ala Leu Met Glu Met Arg His Pro Asn
                820                 825                 830

Ser Val Gln Glu Glu Arg Lys Ser Tyr Lys Val Arg Phe Asn Ser Val
                835                 840                 845

Ser Ser Tyr Ser Asp Ser Arg Lys Ser Ser Gly Asp Gly Pro Asp Leu
                850                 855                 860

Arg Asp Asn Phe Glu Ser Thr Gly Pro Leu Ala Asn Val Arg Phe Ser
865                 870                 875                 880

Val Phe Gly Leu Gly Ser Arg Ala Tyr Pro His Phe Cys Ala Phe Gly
                885                 890                 895

His Ala Val Asp Thr Leu Leu Glu Glu Leu Gly Gly Glu Arg Ile Leu
                900                 905                 910

Lys Met Arg Glu Gly Asp Glu Leu Cys Gly Gln Glu Glu Ala Phe Arg
                915                 920                 925

Thr Trp Ala Lys Lys Val Phe Lys Ala Ala Cys Asp Val Phe Cys Val
                930                 935                 940

Gly Asp Asp Val Asn Ile Glu Lys Pro Asn Asn Ser Leu Ile Ser Asn
```

-continued

```
            945                 950                 955                 960
Asp Arg Ser Trp Lys Arg Asn Lys Phe Arg Leu Thr Tyr Val Ala Glu
                965                 970                 975
Ala Pro Asp Leu Thr Gln Gly Leu Ser Asn Val His Lys Lys Arg Val
        980                 985                 990
Ser Ala Ala Arg Leu Leu Ser Arg Gln Asn Leu Gln Ser Pro Lys Phe
    995                 1000                1005
Ser Arg Ser Thr Ile Phe Val Arg Leu His Thr Asn Gly Asn Gln
    1010                1015                1020
Glu Leu Gln Tyr Gln Pro Gly Asp His Leu Gly Val Phe Pro Gly
    1025                1030                1035
Asn His Glu Asp Leu Val Asn Ala Leu Ile Glu Arg Leu Glu Asp
    1040                1045                1050
Ala Pro Pro Ala Asn His Val Val Lys Val Glu Met Leu Glu Glu
    1055                1060                1065
Arg Asn Thr Ala Leu Gly Val Ile Ser Asn Trp Lys Asp Glu Ser
    1070                1075                1080
Arg Leu Pro Pro Cys Thr Ile Phe Gln Ala Phe Lys Tyr Tyr Leu
    1085                1090                1095
Asp Ile Thr Thr Pro Pro Thr Pro Leu Gln Leu Gln Gln Phe Ala
    1100                1105                1110
Ser Leu Ala Thr Asn Glu Lys Glu Lys Gln Arg Leu Leu Val Leu
    1115                1120                1125
Ser Lys Gly Leu Gln Glu Tyr Glu Glu Trp Lys Trp Gly Lys Asn
    1130                1135                1140
Pro Thr Met Val Glu Val Leu Glu Glu Phe Pro Ser Ile Gln Met
    1145                1150                1155
Pro Ala Thr Leu Leu Leu Thr Gln Leu Ser Leu Leu Gln Pro Arg
    1160                1165                1170
Tyr Tyr Ser Ile Ser Ser Ser Pro Asp Met Tyr Pro Asp Glu Val
    1175                1180                1185
His Leu Thr Val Ala Ile Val Ser Tyr His Thr Arg Asp Gly Glu
    1190                1195                1200
Gly Pro Val His His Gly Val Cys Ser Ser Trp Leu Asn Arg Ile
    1205                1210                1215
Gln Ala Asp Asp Val Val Pro Cys Phe Val Arg Gly Ala Pro Ser
    1220                1225                1230
Phe His Leu Pro Arg Asn Pro Gln Val Pro Cys Ile Leu Val Gly
    1235                1240                1245
Pro Gly Thr Gly Ile Ala Pro Phe Arg Ser Phe Trp Gln Gln Arg
    1250                1255                1260
Gln Phe Asp Ile Gln His Lys Gly Met Asn Pro Cys Pro Met Val
    1265                1270                1275
Leu Val Phe Gly Cys Arg Gln Ser Lys Ile Asp His Ile Tyr Arg
    1280                1285                1290
Glu Glu Thr Leu Gln Ala Lys Asn Lys Gly Val Phe Arg Glu Leu
    1295                1300                1305
Tyr Thr Ala Tyr Ser Arg Glu Pro Asp Arg Pro Lys Lys Tyr Val
    1310                1315                1320
Gln Asp Val Leu Gln Glu Gln Leu Ala Glu Ser Val Tyr Arg Ala
    1325                1330                1335
Leu Lys Glu Gln Gly Gly His Ile Tyr Val Cys Gly Asp Val Thr
    1340                1345                1350
```

-continued

```
Met Ala Ala Asp Val Leu Lys Ala Ile Gln Arg Ile Met Thr Gln
    1355                1360                1365

Gln Gly Lys Leu Ser Glu Glu Asp Ala Gly Val Phe Ile Ser Arg
    1370                1375                1380

Leu Arg Asp Asp Asn Arg Tyr His Glu Asp Ile Phe Gly Val Thr
    1385                1390                1395

Leu Arg Thr Tyr Glu Val Thr Asn Arg Leu Arg Ser Glu Ser Ile
    1400                1405                1410

Ala Phe Ile Glu Glu Ser Lys Lys Asp Ala Asp Glu Val Phe Ser
    1415                1420                1425

Ser

<210> SEQ ID NO 3
<211> LENGTH: 1203
<212> TYPE: PRT
<213> ORGANISM: Homo sapiens

<400> SEQUENCE: 3

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
                20                  25                  30

Thr Pro Ala Pro Glu Pro Ser Arg Ala Pro Ala Ser Leu Leu Pro Pro
            35                  40                  45

Ala Pro Glu His Ser Pro Pro Ser Ser Pro Leu Thr Gln Pro Pro Glu
        50                  55                  60

Gly Pro Lys Phe Pro Arg Val Lys Asn Trp Glu Val Gly Ser Ile Thr
65                  70                  75                  80

Tyr Asp Thr Leu Ser Ala Gln Ala Gln Gln Asp Gly Pro Cys Thr Pro
                85                  90                  95

Arg Arg Cys Leu Gly Ser Leu Val Phe Pro Arg Lys Leu Gln Gly Arg
                100                 105                 110

Pro Ser Pro Gly Pro Pro Ala Pro Glu Gln Leu Leu Ser Gln Ala Arg
            115                 120                 125

Asp Phe Ile Asn Gln Tyr Tyr Ser Ser Ile Lys Arg Ser Gly Ser Gln
        130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
                180                 185                 190

Leu Gln Val Phe Asp Ala Arg Asp Cys Arg Ser Ala Gln Glu Met Phe
            195                 200                 205

Thr Tyr Ile Cys Asn His Ile Lys Tyr Ala Thr Asn Arg Gly Asn Leu
        210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
                260                 265                 270

Leu Cys Ile Gln His Gly Trp Thr Pro Gly Asn Gly Arg Phe Asp Val
            275                 280                 285
```

```
Leu Pro Leu Leu Leu Gln Ala Pro Asp Glu Pro Pro Glu Leu Phe Leu
    290                 295                 300
Leu Pro Pro Glu Leu Val Leu Glu Val Pro Leu Glu His Pro Thr Leu
305                 310                 315                 320
Glu Trp Phe Ala Ala Leu Gly Leu Arg Trp Tyr Ala Leu Pro Ala Val
                325                 330                 335
Ser Asn Met Leu Leu Glu Ile Gly Gly Leu Glu Phe Pro Ala Ala Pro
            340                 345                 350
Phe Ser Gly Trp Tyr Met Ser Thr Glu Ile Gly Thr Arg Asn Leu Cys
            355                 360                 365
Asp Pro His Arg Tyr Asn Ile Leu Glu Asp Val Ala Val Cys Met Asp
    370                 375                 380
Leu Asp Thr Arg Thr Thr Ser Ser Leu Trp Lys Asp Lys Ala Ala Val
385                 390                 395                 400
Glu Ile Asn Val Ala Val Leu His Ser Tyr Gln Leu Ala Lys Val Thr
                405                 410                 415
Ile Val Asp His His Ala Ala Thr Ala Ser Phe Met Lys His Leu Glu
            420                 425                 430
Asn Glu Gln Lys Ala Arg Gly Gly Cys Pro Ala Asp Trp Ala Trp Ile
            435                 440                 445
Val Pro Pro Ile Ser Gly Ser Leu Thr Pro Val Phe His Gln Glu Met
    450                 455                 460
Val Asn Tyr Phe Leu Ser Pro Ala Phe Arg Tyr Gln Pro Asp Pro Trp
465                 470                 475                 480
Lys Gly Ser Ala Ala Lys Gly Thr Gly Ile Thr Arg Lys Lys Thr Phe
                485                 490                 495
Lys Glu Val Ala Asn Ala Val Lys Ile Ser Ala Ser Leu Met Gly Thr
            500                 505                 510
Val Met Ala Lys Arg Val Lys Ala Thr Ile Leu Tyr Gly Ser Glu Thr
            515                 520                 525
Gly Arg Ala Gln Ser Tyr Ala Gln Gln Leu Gly Arg Leu Phe Arg Lys
    530                 535                 540
Ala Phe Asp Pro Arg Val Leu Cys Met Asp Glu Tyr Asp Val Val Ser
545                 550                 555                 560
Leu Glu His Glu Thr Leu Val Leu Val Val Thr Ser Thr Phe Gly Asn
                565                 570                 575
Gly Asp Pro Pro Glu Asn Gly Ser Phe Ala Ala Leu Met Glu
            580                 585                 590
Met Ser Gly Pro Tyr Asn Ser Ser Pro Arg Pro Glu Gln His Lys Ser
            595                 600                 605
Tyr Lys Ile Arg Phe Asn Ser Ile Ser Cys Ser Asp Pro Leu Val Ser
    610                 615                 620
Ser Trp Arg Arg Lys Arg Lys Glu Ser Ser Asn Thr Asp Ser Ala Gly
625                 630                 635                 640
Ala Leu Gly Thr Leu Arg Phe Cys Val Phe Gly Leu Gly Ser Arg Ala
                645                 650                 655
Tyr Pro His Phe Cys Ala Phe Ala Arg Ala Val Asp Thr Arg Leu Glu
            660                 665                 670
Glu Leu Gly Gly Glu Arg Leu Leu Gln Leu Gly Gln Gly Asp Glu Leu
            675                 680                 685
Cys Gly Gln Glu Glu Ala Phe Arg Gly Trp Ala Gln Ala Ala Phe Gln
    690                 695                 700
```

-continued

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
            725                 730                 735

Leu Ser Ala Gln Ala Glu Gly Leu Gln Leu Leu Pro Gly Leu Ile His
        740                 745                 750

Val His Arg Arg Lys Met Phe Gln Ala Thr Ile Arg Ser Val Glu Asn
            755                 760                 765

Leu Gln Ser Ser Lys Ser Thr Arg Ala Thr Ile Leu Val Arg Leu Asp
        770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
            820                 825                 830

Glu Lys Gly Ser Pro Gly Gly Pro Pro Pro Gly Trp Val Arg Asp Pro
        835                 840                 845

Arg Leu Pro Pro Cys Thr Leu Arg Gln Ala Leu Thr Phe Phe Leu Asp
850                 855                 860

Ile Thr Ser Pro Ser Pro Gln Leu Leu Arg Leu Leu Ser Thr Leu
865                 870                 875                 880

Ala Glu Glu Pro Arg Glu Gln Gln Glu Leu Glu Ala Leu Ser Gln Asp
                885                 890                 895

Pro Arg Arg Tyr Glu Glu Trp Lys Trp Phe Arg Cys Pro Thr Leu Leu
            900                 905                 910

Glu Val Leu Glu Gln Phe Pro Ser Val Ala Leu Pro Ala Pro Leu Leu
        915                 920                 925

Leu Thr Gln Leu Pro Leu Leu Gln Pro Arg Tyr Tyr Ser Val Ser Ser
        930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
            965                 970                 975

Ser Thr Trp Leu Ser Gln Leu Lys Pro Gly Asp Pro Val Pro Cys Phe
        980                 985                 990

Ile Arg Gly Ala Pro Ser Phe Arg  Leu Pro Pro Asp Pro  Ser Leu Pro
    995                 1000                1005

Cys Ile Leu Val Gly Pro Gly  Thr Gly Ile Ala Pro  Phe Arg Gly
    1010                1015                1020

Phe Trp Gln Glu Arg Leu His  Asp Ile Glu Ser Lys  Gly Leu Gln
    1025                1030                1035

Pro Thr Pro Met Thr Leu Val  Phe Gly Cys Arg Cys  Ser Gln Leu
    1040                1045                1050

Asp His Leu Tyr Arg Asp Glu  Val Gln Asn Ala Gln  Gln Arg Gly
    1055                1060                1065

Val Phe Gly Arg Val Leu Thr  Ala Phe Ser Arg Glu  Pro Asp Asn
    1070                1075                1080

Pro Lys Thr Tyr Val Gln Asp  Ile Leu Arg Thr Glu  Leu Ala Ala
    1085                1090                1095

Glu Val His Arg Val Leu Cys  Leu Glu Arg Gly His  Met Phe Val
    1100                1105                1110

Cys Gly Asp Val Thr Met Ala  Thr Asn Val Leu Gln  Thr Val Gln

-continued

```
            1115                1120                1125

Arg Ile Leu Ala Thr Glu Gly Asp Met Glu Leu Asp Glu Ala Gly
    1130                1135                1140

Asp Val Ile Gly Val Leu Arg Asp Gln Gln Arg Tyr His Glu Asp
    1145                1150                1155

Ile Phe Gly Leu Thr Leu Arg Thr Gln Glu Val Thr Ser Arg Ile
    1160                1165                1170

Arg Thr Gln Ser Phe Ser Leu Gln Glu Arg Gln Leu Arg Gly Ala
    1175                1180                1185

Val Pro Trp Ala Phe Asp Pro Pro Gly Ser Asp Thr Asn Ser Pro
    1190                1195                1200

<210> SEQ ID NO 4
<211> LENGTH: 1153
<212> TYPE: PRT
<213> ORGANISM: Homo sapiens

<400> SEQUENCE: 4

Met Ala Cys Pro Trp Lys Phe Leu Phe Lys Thr Lys Phe His Gln Tyr
1               5                   10                  15

Ala Met Asn Gly Glu Lys Asp Ile Asn Asn Val Glu Lys Ala Pro
            20                  25                  30

Cys Ala Thr Ser Ser Pro Val Thr Gln Asp Leu Gln Tyr His Asn
            35                  40                  45

Leu Ser Lys Gln Gln Asn Glu Ser Pro Gln Pro Leu Val Glu Thr Gly
        50                  55                  60

Lys Lys Ser Pro Glu Ser Leu Val Lys Leu Asp Ala Thr Pro Leu Ser
65                  70                  75                  80

Ser Pro Arg His Val Arg Ile Lys Asn Trp Gly Ser Gly Met Thr Phe
                85                  90                  95

Gln Asp Thr Leu His His Lys Ala Lys Gly Ile Leu Thr Cys Arg Ser
            100                 105                 110

Lys Ser Cys Leu Gly Ser Ile Met Thr Pro Lys Ser Leu Thr Arg Gly
            115                 120                 125

Pro Arg Asp Lys Pro Thr Pro Pro Asp Glu Leu Leu Pro Gln Ala Ile
        130                 135                 140

Glu Phe Val Asn Gln Tyr Tyr Gly Ser Phe Lys Glu Ala Lys Ile Glu
145                 150                 155                 160

Glu His Leu Ala Arg Val Glu Ala Val Thr Lys Glu Ile Glu Thr Thr
                165                 170                 175

Gly Thr Tyr Gln Leu Thr Gly Asp Glu Leu Ile Phe Ala Thr Lys Gln
            180                 185                 190

Ala Trp Arg Asn Ala Pro Arg Cys Ile Gly Arg Ile Gln Trp Ser Asn
        195                 200                 205

Leu Gln Val Phe Asp Ala Arg Ser Cys Ser Thr Ala Arg Glu Met Phe
    210                 215                 220

Glu His Ile Cys Arg His Val Arg Tyr Ser Thr Asn Asn Gly Asn Ile
225                 230                 235                 240

Arg Ser Ala Ile Thr Val Phe Pro Gln Arg Ser Asp Gly Lys His Asp
                245                 250                 255

Phe Arg Val Trp Asn Ala Gln Leu Ile Arg Tyr Ala Gly Tyr Gln Met
            260                 265                 270

Pro Asp Gly Ser Ile Arg Gly Asp Pro Ala Asn Val Glu Phe Thr Gln
        275                 280                 285
```

```
Leu Cys Ile Asp Leu Gly Trp Lys Pro Lys Tyr Gly Arg Phe Asp Val
    290                 295                 300

Val Pro Leu Val Leu Gln Ala Asn Gly Arg Asp Pro Glu Leu Phe Glu
305                 310                 315                 320

Ile Pro Pro Asp Leu Val Leu Glu Val Ala Met Glu His Pro Lys Tyr
                325                 330                 335

Glu Trp Phe Arg Glu Leu Glu Leu Lys Trp Tyr Ala Leu Pro Ala Val
            340                 345                 350

Ala Asn Met Leu Leu Glu Val Gly Gly Leu Glu Phe Pro Gly Cys Pro
                355                 360                 365

Phe Asn Gly Trp Tyr Met Gly Thr Glu Ile Gly Val Arg Asp Phe Cys
    370                 375                 380

Asp Val Gln Arg Tyr Asn Ile Leu Glu Glu Val Gly Arg Arg Met Gly
385                 390                 395                 400

Leu Glu Thr His Lys Leu Ala Ser Leu Trp Lys Asp Gln Ala Val Val
                405                 410                 415

Glu Ile Asn Ile Ala Val Leu His Ser Phe Gln Lys Gln Asn Val Thr
            420                 425                 430

Ile Met Asp His His Ser Ala Ala Glu Ser Phe Met Lys Tyr Met Gln
                435                 440                 445

Asn Glu Tyr Arg Ser Arg Gly Gly Cys Pro Ala Asp Trp Ile Trp Leu
    450                 455                 460

Val Pro Pro Met Ser Gly Ser Ile Thr Pro Val Phe His Gln Glu Met
465                 470                 475                 480

Leu Asn Tyr Val Leu Ser Pro Phe Tyr Tyr Gln Val Glu Ala Trp
                485                 490                 495

Lys Thr His Val Trp Gln Asp Glu Lys Arg Arg Pro Lys Arg Arg Glu
                500                 505                 510

Ile Pro Leu Lys Val Leu Val Lys Ala Val Leu Phe Ala Cys Met Leu
            515                 520                 525

Met Arg Lys Thr Met Ala Ser Arg Val Arg Val Thr Ile Leu Phe Ala
    530                 535                 540

Thr Glu Thr Gly Lys Ser Glu Ala Leu Ala Trp Asp Leu Gly Ala Leu
545                 550                 555                 560

Phe Ser Cys Ala Phe Asn Pro Lys Val Val Cys Met Asp Lys Tyr Arg
                565                 570                 575

Leu Ser Cys Leu Glu Glu Glu Arg Leu Leu Leu Val Val Thr Ser Thr
            580                 585                 590

Phe Gly Asn Gly Asp Cys Pro Gly Asn Gly Glu Lys Leu Lys Lys Ser
    595                 600                 605

Leu Phe Met Leu Lys Glu Leu Asn Asn Lys Phe Arg Tyr Ala Val Phe
    610                 615                 620

Gly Leu Gly Ser Ser Met Tyr Pro Arg Phe Cys Ala Phe Ala His Asp
625                 630                 635                 640

Ile Asp Gln Lys Leu Ser His Leu Gly Ala Ser Gln Leu Thr Pro Met
                645                 650                 655

Gly Glu Gly Asp Glu Leu Ser Gly Gln Glu Asp Ala Phe Arg Ser Trp
                660                 665                 670

Ala Val Gln Ile Phe Lys Ala Ala Cys Glu Thr Phe Asp Val Arg Gly
                675                 680                 685

Lys Gln His Ile Gln Ile Pro Lys Leu Tyr Thr Ser Asn Val Thr Trp
    690                 695                 700

Asp Pro His His Tyr Arg Leu Val Gln Asp Ser Gln Pro Leu Asp Leu
```

-continued

```
705                 710                 715                 720
Ser Lys Ala Leu Ser Ser Met His Ala Lys Asn Val Phe Thr Met Arg
                725                 730                 735
Leu Lys Ser Arg Gln Asn Leu Gln Ser Pro Thr Ser Ser Arg Ala Thr
                740                 745                 750
Ile Leu Val Glu Leu Ser Cys Glu Asp Gly Gln Gly Leu Asn Tyr Leu
                755                 760                 765
Pro Gly Glu His Leu Gly Val Cys Pro Gly Asn Gln Pro Ala Leu Val
                770                 775                 780
Gln Gly Ile Leu Glu Arg Val Val Asp Gly Pro Thr Pro His Gln Thr
785                 790                 795                 800
Val Arg Leu Glu Ala Leu Asp Glu Ser Gly Ser Tyr Trp Val Ser Asp
                805                 810                 815
Lys Arg Leu Pro Pro Cys Ser Leu Ser Gln Ala Leu Thr Tyr Phe Leu
                820                 825                 830
Asp Ile Thr Thr Pro Thr Gln Leu Leu Leu Gln Lys Leu Ala Gln
                835                 840                 845
Val Ala Thr Glu Glu Pro Glu Arg Gln Arg Leu Glu Ala Leu Cys Gln
                850                 855                 860
Pro Ser Glu Tyr Ser Lys Trp Lys Phe Thr Asn Ser Pro Thr Phe Leu
865                 870                 875                 880
Glu Val Leu Glu Glu Phe Pro Ser Leu Arg Val Ser Ala Gly Phe Leu
                885                 890                 895
Leu Ser Gln Leu Pro Ile Leu Lys Pro Arg Phe Tyr Ser Ile Ser Ser
                900                 905                 910
Ser Arg Asp His Thr Pro Thr Glu Ile His Leu Thr Val Ala Val Val
                915                 920                 925
Thr Tyr His Thr Gly Asp Gly Gln Gly Pro Leu His His Gly Val Cys
                930                 935                 940
Ser Thr Trp Leu Asn Ser Leu Lys Pro Gln Asp Pro Val Pro Cys Phe
945                 950                 955                 960
Val Arg Asn Ala Ser Ala Phe His Leu Pro Glu Asp Pro Ser His Pro
                965                 970                 975
Cys Ile Leu Ile Gly Pro Gly Thr Gly Ile Ala Pro Phe Arg Ser Phe
                980                 985                 990
Trp Gln Gln Arg Leu His Asp Ser Gln His Lys Gly Val Arg Gly Gly
                995                 1000                1005
Arg Met Thr Leu Val Phe Gly Cys Arg Arg Pro Asp Glu Asp His
                1010                1015                1020
Ile Tyr Gln Glu Glu Met Leu Glu Met Ala Gln Lys Gly Val Leu
                1025                1030                1035
His Ala Val His Thr Ala Tyr Ser Arg Leu Pro Gly Lys Pro Lys
                1040                1045                1050
Val Tyr Val Gln Asp Ile Leu Arg Gln Gln Leu Ala Ser Glu Val
                1055                1060                1065
Leu Arg Val Leu His Lys Glu Pro Gly His Leu Tyr Val Cys Gly
                1070                1075                1080
Asp Val Arg Met Ala Arg Asp Val Ala His Thr Leu Lys Gln Leu
                1085                1090                1095
Val Ala Ala Lys Leu Lys Leu Asn Glu Glu Gln Val Glu Asp Tyr
                1100                1105                1110
Phe Phe Gln Leu Lys Ser Gln Lys Arg Tyr His Glu Asp Ile Phe
                1115                1120                1125
```

-continued

Gly Ala Val Phe Pro Tyr Glu Ala Lys Lys Asp Arg Val Ala Val
        1130                1135                1140

Gln Pro Ser Ser Leu Glu Met Ser Ala Leu
        1145                1150

<210> SEQ ID NO 5
<211> LENGTH: 1144
<212> TYPE: PRT
<213> ORGANISM: Mus musculus

<400> SEQUENCE: 5

Met Ala Cys Pro Trp Lys Phe Leu Phe Lys Val Lys Ser Tyr Gln Ser
1               5                   10                  15

Asp Leu Lys Glu Lys Asp Ile Asn Asn Val Lys Lys Thr Pro
            20                  25                  30

Cys Ala Val Leu Ser Pro Thr Ile Gln Asp Asp Pro Lys Ser His Gln
        35                  40                  45

Asn Gly Ser Pro Gln Leu Leu Thr Gly Thr Ala Gln Asn Val Pro Glu
    50                  55                  60

Ser Leu Asp Lys Leu His Val Thr Ser Thr Arg Pro Gln Tyr Val Arg
65                  70                  75                  80

Ile Lys Asn Trp Gly Ser Gly Glu Ile Leu His Asp Thr Leu His His
                85                  90                  95

Lys Ala Thr Ser Asp Phe Thr Cys Lys Ser Lys Ser Cys Leu Gly Ser
            100                 105                 110

Ile Met Asn Pro Lys Ser Leu Thr Arg Gly Pro Arg Asp Lys Pro Thr
        115                 120                 125

Pro Leu Glu Glu Leu Leu Pro His Ala Ile Glu Phe Ile Asn Gln Tyr
    130                 135                 140

Tyr Gly Ser Phe Lys Glu Ala Lys Ile Glu Glu His Leu Ala Arg Leu
145                 150                 155                 160

Glu Ala Val Thr Lys Glu Ile Glu Thr Thr Gly Thr Tyr Gln Leu Thr
                165                 170                 175

Leu Asp Glu Leu Ile Phe Ala Thr Lys Met Ala Trp Arg Asn Ala Pro
            180                 185                 190

Arg Cys Ile Gly Arg Ile Gln Trp Ser Asn Leu Gln Val Phe Asp Ala
        195                 200                 205

Arg Asn Cys Ser Thr Ala Gln Glu Met Phe Gln His Ile Cys Arg His
    210                 215                 220

Ile Leu Tyr Ala Thr Asn Asn Gly Asn Ile Arg Ser Ala Ile Thr Val
225                 230                 235                 240

Phe Pro Gln Arg Ser Asp Gly Lys His Asp Phe Arg Leu Trp Asn Ser
                245                 250                 255

Gln Leu Ile Arg Tyr Ala Gly Tyr Gln Met Pro Asp Gly Thr Ile Arg
            260                 265                 270

Gly Asp Ala Ala Thr Leu Glu Phe Thr Gln Leu Cys Ile Asp Leu Gly
        275                 280                 285

Trp Lys Pro Arg Tyr Gly Arg Phe Asp Val Leu Pro Leu Val Leu Gln
    290                 295                 300

Ala Asp Gly Gln Asp Pro Glu Val Phe Glu Ile Pro Pro Asp Leu Val
305                 310                 315                 320

Leu Glu Val Thr Met Glu His Pro Lys Tyr Glu Trp Phe Gln Glu Leu
                325                 330                 335

Gly Leu Lys Trp Tyr Ala Leu Pro Ala Val Ala Asn Met Leu Leu Glu

-continued

```
                340             345             350
    Val Gly Gly Leu Glu Phe Pro Ala Cys Pro Phe Asn Gly Trp Tyr Met
                355             360             365
    Gly Thr Glu Ile Gly Val Arg Asp Phe Cys Asp Thr Gln Arg Tyr Asn
            370             375             380
    Ile Leu Glu Glu Val Gly Arg Arg Met Gly Leu Glu Thr His Thr Leu
385             390             395             400
    Ala Ser Leu Trp Lys Asp Arg Ala Val Thr Glu Ile Asn Val Ala Val
                405             410             415
    Leu His Ser Phe Gln Lys Gln Asn Val Thr Ile Met Asp His His Thr
                420             425             430
    Ala Ser Glu Ser Phe Met Lys His Met Gln Asn Glu Tyr Arg Ala Arg
                435             440             445
    Gly Gly Cys Pro Ala Asp Trp Ile Trp Leu Val Pro Pro Val Ser Gly
                450             455             460
    Ser Ile Thr Pro Val Phe His Gln Glu Met Leu Asn Tyr Val Leu Ser
465             470             475             480
    Pro Phe Tyr Tyr Tyr Gln Ile Glu Pro Trp Lys Thr His Ile Trp Gln
                485             490             495
    Asn Glu Lys Leu Arg Pro Arg Arg Glu Ile Arg Phe Arg Val Leu
                500             505             510
    Val Lys Val Phe Phe Ala Ser Met Leu Met Arg Lys Val Met Ala
                515             520             525
    Ser Arg Val Arg Ala Thr Val Leu Phe Ala Thr Glu Thr Gly Lys Ser
                530             535             540
    Glu Ala Leu Ala Arg Asp Leu Ala Thr Leu Phe Ser Tyr Ala Phe Asn
545             550             555             560
    Thr Lys Val Val Cys Met Asp Gln Tyr Lys Ala Ser Thr Leu Glu Glu
                565             570             575
    Glu Gln Leu Leu Leu Val Val Thr Ser Thr Phe Gly Asn Gly Asp Cys
                580             585             590
    Pro Ser Asn Gly Gln Thr Leu Lys Lys Ser Leu Phe Met Leu Arg Glu
                595             600             605
    Leu Asn His Thr Phe Arg Tyr Ala Val Phe Gly Leu Gly Ser Ser Met
                610             615             620
    Tyr Pro Gln Phe Cys Ala Phe Ala His Asp Ile Asp Gln Lys Leu Ser
625             630             635             640
    His Leu Gly Ala Ser Gln Leu Ala Pro Thr Gly Glu Gly Asp Glu Leu
                645             650             655
    Ser Gly Gln Glu Asp Ala Phe Arg Ser Trp Ala Val Gln Thr Phe Arg
                660             665             670
    Ala Ala Cys Glu Thr Phe Asp Val Arg Ser Lys His His Ile Gln Ile
                675             680             685
    Pro Lys Arg Phe Thr Ser Asn Ala Thr Trp Glu Pro Gln Gln Tyr Arg
                690             695             700
    Leu Ile Gln Ser Pro Glu Pro Leu Asp Leu Asn Arg Ala Leu Ser Ser
705             710             715             720
    Ile His Ala Lys Asn Val Phe Thr Met Arg Leu Lys Ser Gln Gln Asn
                725             730             735
    Leu Gln Ser Glu Lys Ser Ser Arg Thr Thr Leu Leu Val Gln Leu Thr
                740             745             750
    Phe Glu Gly Ser Arg Gly Pro Ser Tyr Leu Pro Gly Glu His Leu Gly
                755             760             765
```

-continued

```
Ile Phe Pro Gly Asn Gln Thr Ala Leu Val Gln Gly Ile Leu Glu Arg
    770                 775                 780
Val Val Asp Cys Pro Thr Pro His Gln Thr Val Cys Leu Glu Val Leu
785                 790                 795                 800
Asp Glu Ser Gly Ser Tyr Trp Val Lys Asp Lys Arg Leu Pro Pro Cys
            805                 810                 815
Ser Leu Ser Gln Ala Leu Thr Tyr Phe Leu Asp Ile Thr Thr Pro Pro
            820                 825                 830
Thr Gln Leu Gln Leu His Lys Leu Ala Arg Phe Ala Thr Asp Glu Thr
            835                 840                 845
Asp Arg Gln Arg Leu Glu Ala Leu Cys Gln Pro Ser Glu Tyr Asn Asp
850                 855                 860
Trp Lys Phe Ser Asn Asn Pro Thr Phe Leu Glu Val Leu Glu Glu Phe
865                 870                 875                 880
Pro Ser Leu His Val Pro Ala Ala Phe Leu Ser Gln Leu Pro Ile
            885                 890                 895
Leu Lys Pro Arg Tyr Tyr Ser Ile Ser Ser Ser Gln Asp His Thr Pro
            900                 905                 910
Ser Glu Val His Leu Thr Val Ala Val Val Thr Tyr Arg Thr Arg Asp
            915                 920                 925
Gly Gln Gly Pro Leu His His Gly Val Cys Ser Thr Trp Ile Arg Asn
            930                 935                 940
Leu Lys Pro Gln Asp Pro Val Pro Cys Phe Val Arg Ser Val Ser Gly
945                 950                 955                 960
Phe Gln Leu Pro Glu Asp Pro Ser Gln Pro Cys Ile Leu Ile Gly Pro
            965                 970                 975
Gly Thr Gly Ile Ala Pro Phe Arg Ser Phe Trp Gln Gln Arg Leu His
            980                 985                 990
Asp Ser Gln His Lys Gly Leu Lys Gly Gly Arg Met Ser Leu Val Phe
            995                 1000                1005
Gly Cys Arg His Pro Glu Glu Asp His Leu Tyr Gln Glu Glu Met
    1010                1015                1020
Gln Glu Met Val Arg Lys Arg Val Leu Phe Gln Val His Thr Gly
    1025                1030                1035
Tyr Ser Arg Leu Pro Gly Lys Pro Lys Val Tyr Val Gln Asp Ile
    1040                1045                1050
Leu Gln Lys Gln Leu Ala Asn Glu Val Leu Ser Val Leu His Gly
    1055                1060                1065
Glu Gln Gly His Leu Tyr Ile Cys Gly Asp Val Arg Met Ala Arg
    1070                1075                1080
Asp Val Ala Thr Thr Leu Lys Lys Leu Val Ala Thr Lys Leu Asn
    1085                1090                1095
Leu Ser Glu Glu Gln Val Glu Asp Tyr Phe Phe Gln Leu Lys Ser
    1100                1105                1110
Gln Lys Arg Tyr His Glu Asp Ile Phe Gly Ala Val Phe Ser Tyr
    1115                1120                1125
Gly Ala Lys Lys Gly Ser Ala Leu Glu Glu Pro Lys Ala Thr Arg
    1130                1135                1140
Leu
```

<210> SEQ ID NO 6
<211> LENGTH: 36
<212> TYPE: DNA

-continued

```
<213> ORGANISM: Artificial Sequence
<220> FEATURE:
<223> OTHER INFORMATION: W409F-NheI-sense PCR primer for site-directed
      mutagenesis of rat nNOS gene.

<400> SEQUENCE: 6
gcatgccttc cggaacgcta gccgatgtgt gggcag                              36

<210> SEQ ID NO 7
<211> LENGTH: 36
<212> TYPE: DNA
<213> ORGANISM: Artificial Sequence
<220> FEATURE:
<223> OTHER INFORMATION: W409F-antisense PCR primer for site-directed
      mutagenesis of rat nNOS gene.

<400> SEQUENCE: 7
ctgcccacac atcggctagc gttccggaag gcatgc                              36

<210> SEQ ID NO 8
<211> LENGTH: 36
<212> TYPE: DNA
<213> ORGANISM: Artificial Sequence
<220> FEATURE:
<223> OTHER INFORMATION: 409YNheI-sense PCR primer for site-directed
      mutagenesis of rat nNOS gene.

<400> SEQUENCE: 8
gcatgcctac cggaacgcta gccgatgtgt gggcag                              36

<210> SEQ ID NO 9
<211> LENGTH: 36
<212> TYPE: DNA
<213> ORGANISM: Artificial Sequence
<220> FEATURE:
<223> OTHER INFORMATION: W409Y-antisense PCR primer for site-directed
      mutagenesis of rat nNOS gene.

<400> SEQUENCE: 9
ctgcccacac atcggctagc gttccggtag gcatgc                              36
```